(12) United States Patent
Doyle, Sr.

(10) Patent No.: US 6,175,767 B1
(45) Date of Patent: Jan. 16, 2001

(54) MULTICHANNEL IMPLANTABLE INNER EAR STIMULATOR

(76) Inventor: James H. Doyle, Sr., 2003 Ivy Hill La., Orange, CA (US) 92867

(*) Notice: Under 35 U.S.C. 154(b), the term of this patent shall be extended for 0 days.

(21) Appl. No.: 09/282,363

(22) Filed: Mar. 31, 1999

Related U.S. Application Data

(60) Provisional application No. 60/080,268, filed on Apr. 1, 1998.

(51) Int. Cl.$^7$ .............................. A61N 1/36; H04R 25/00
(52) U.S. Cl. ................................................................ 607/57
(58) Field of Search ......................................... 607/55–57

(56) References Cited

U.S. PATENT DOCUMENTS

| | | |
|---|---|---|
| 3,449,768 | 6/1969 | Doyle . |
| 4,400,590 | 8/1983 | Michelson . |
| 4,532,930 | 8/1985 | Crosby et al. . |
| 4,711,243 | * 12/1987 | Schafer . |
| 5,443,493 | 8/1995 | Byers et al. . |
| 5,496,369 | 3/1996 | Howard, III . |
| 5,531,774 | 7/1996 | Schulman et al. . |
| 5,549,658 | 8/1996 | Shannon et al. . |
| 5,569,307 | 10/1996 | Schulman et al. . |
| 5,584,869 | 12/1996 | Heck et al. . |
| 5,601,617 | 2/1997 | Loeb et al. . |
| 5,649,970 | 7/1997 | Loeb et al. . |
| 5,674,264 | 10/1997 | Carter et al. . |

OTHER PUBLICATIONS

Doyle, James H.,(1997) "The Auditory System in Humans", ENT–Ear, Nose & Throat Journal, vol. 76, No. 3:122–125.
Doyle, James H. et al., (1964) "Electrical Stimulation of Eighth Cranial Nerve", Archives Of Otolaryngology, vol. 80, 388–391.
Doyle, John Jr. et al., (1963) "Electrical Stimulation In Eighth Nerve Deafness", The Bulletin of The Los Angeles Neurological Society, vol. 28, No. 3, 148–150.

(Dec. 21, 1962) "Direct Wire To Deaf Inner Ear", Medical World News, 24.

* cited by examiner

Primary Examiner—Carl H. Layno
(74) Attorney, Agent, or Firm—Scully, Scott, Murphy & Presser

(57) ABSTRACT

A device is described for stimulating the auditory transmission branch of the $8^{th}$ nerve. It uses electrodes designed to restrict the electrical field to the region of their respective nerve fiber group and produce a gradient field for each channel such that the latency characteristics of the nerve fibers in a given channel will cause a sequential firing (streaming) of the nerve fibers during a portion of the channel stimulus pulse. In the analog system the nerve fiber channels are stimulated in sequence but with their stimulus overlapping their previous channel by an amount equal to the shortest latency period of said channel. During the period when a stimulus pulse is causing nerve fiber streaming the pulse amplitude is modulated with the audio information. In addition during the nerve fiber streaming either electrical means or the shape of the probe compensate for the strength-duration characteristics of the individual nerve fibers. In the digital system there is no streaming as there is a single firing time for nerve fibers in a channel. The channel overlap exists over a number of channels and the audio modulation is in the form of frequency modulation of the channel sequence frequency.

32 Claims, 30 Drawing Sheets

Stimulus Slope to Compensate for Strength Duration Curve

Channel Nerve Activity

FIG. 7
ANALOG PROBE
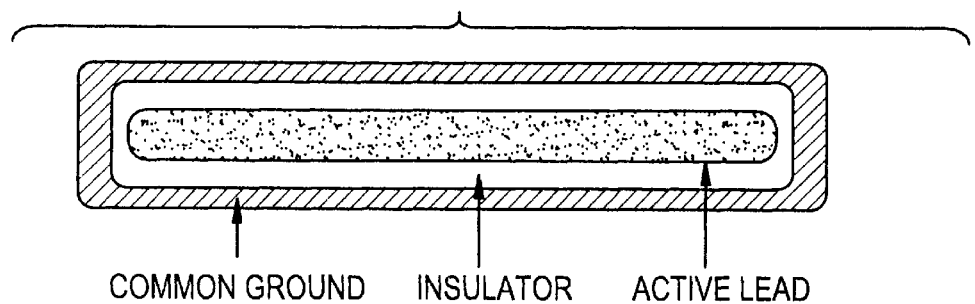
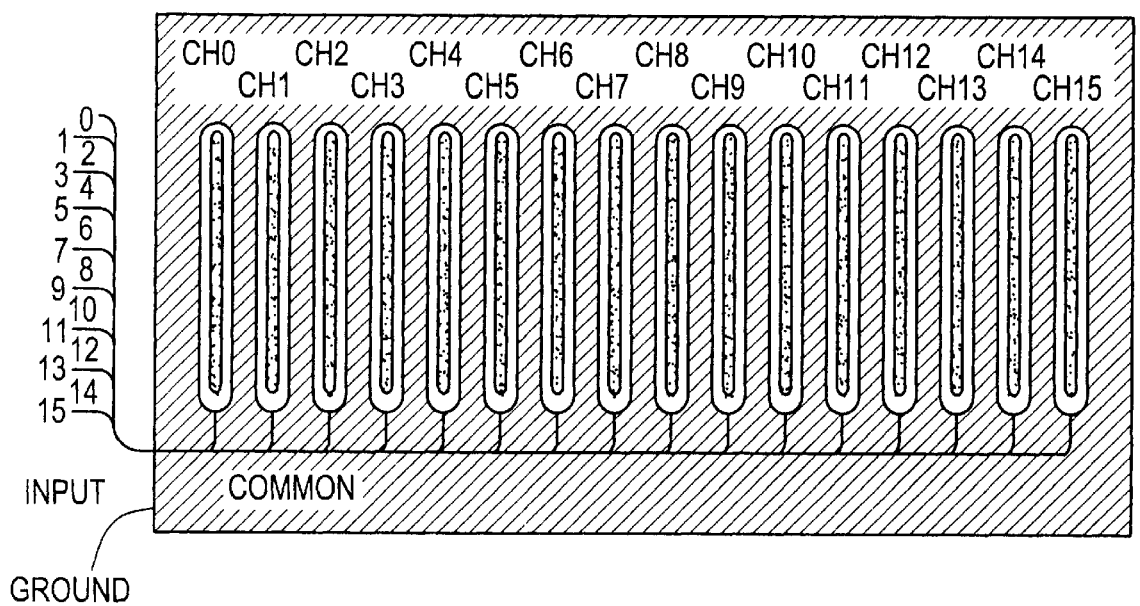

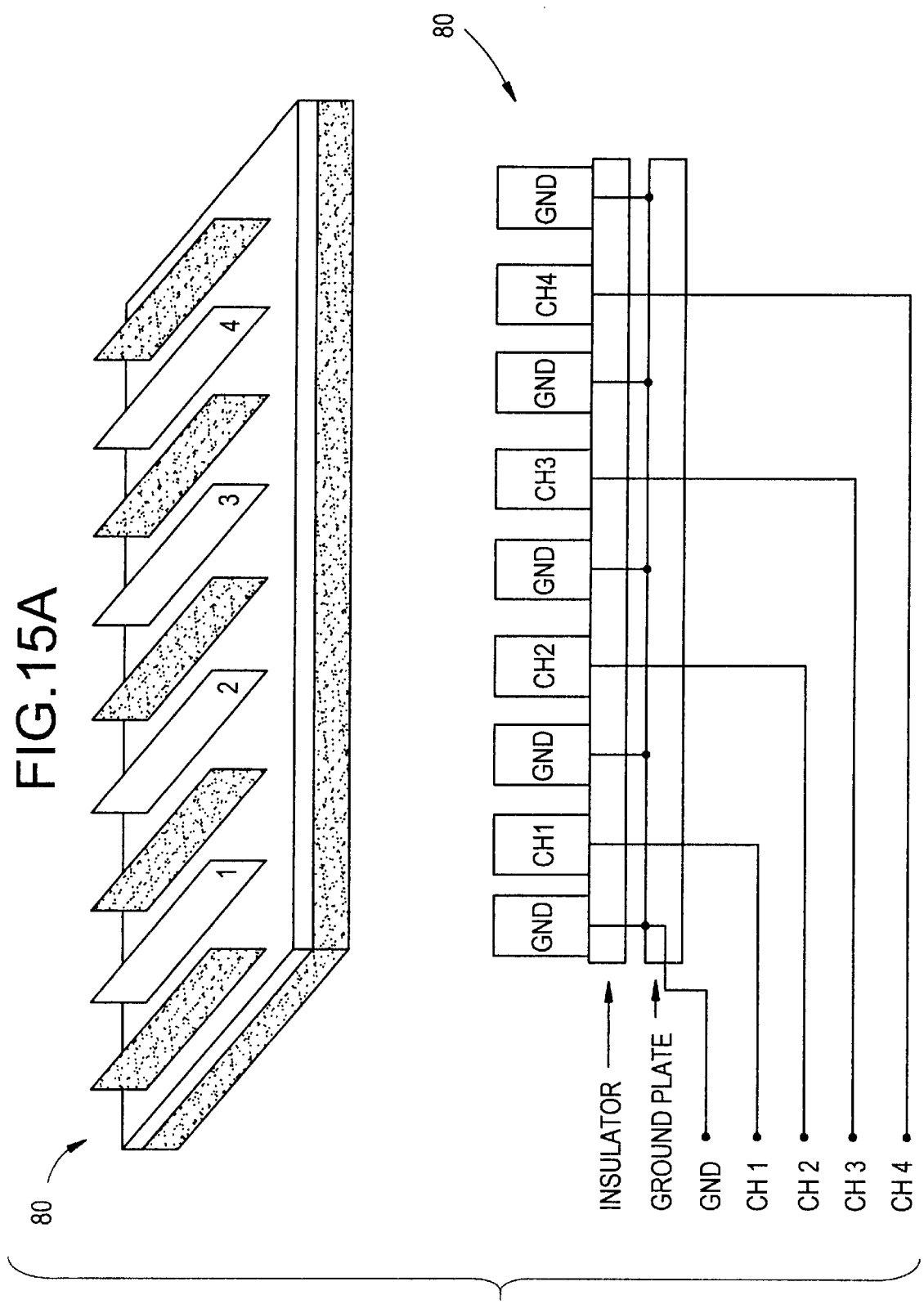

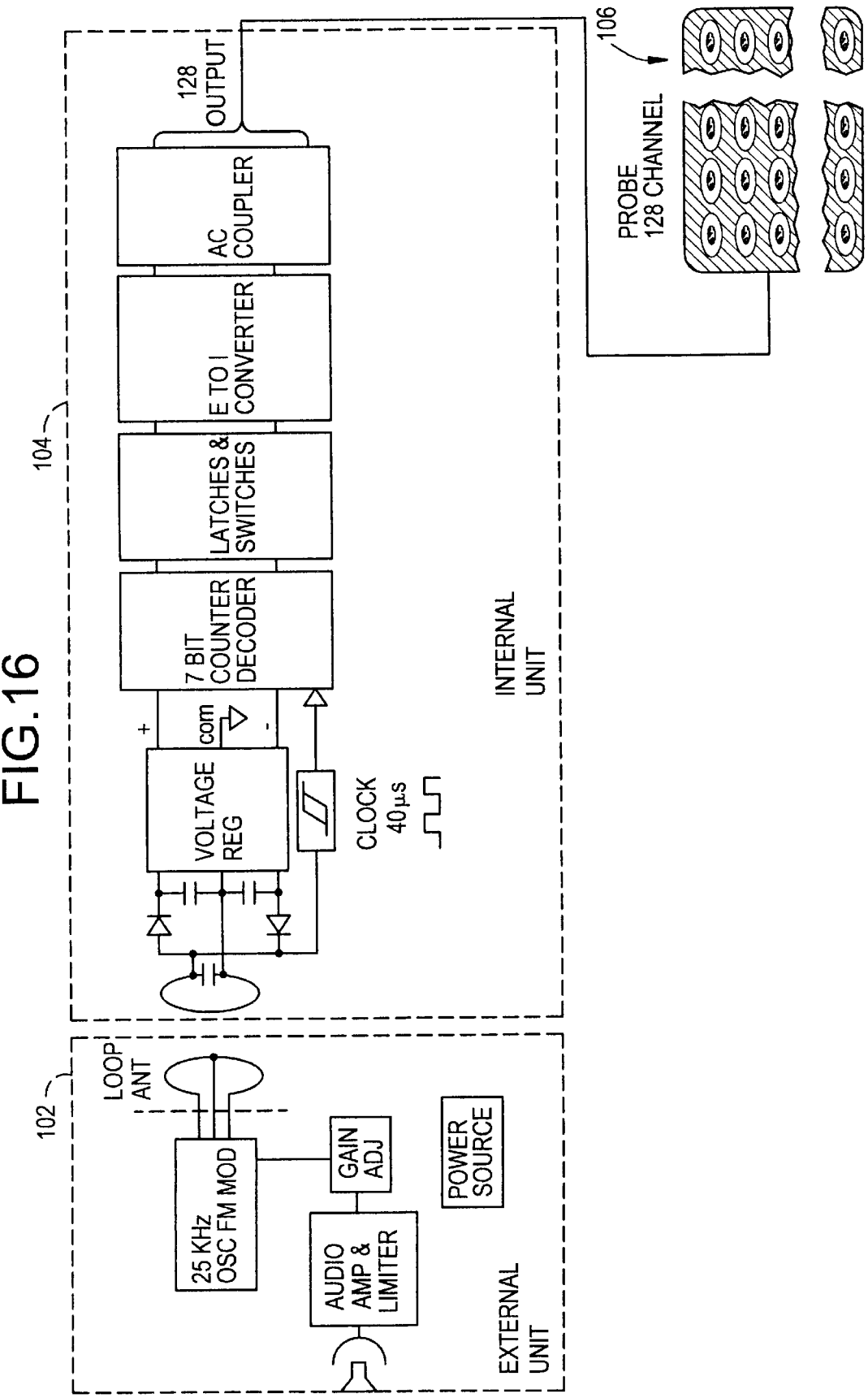

MULTICHANNEL IMPLANTABLE INNER EAR STIMULATOR

CROSS REFERENCE TO RELATED APPLICATION

This application claims priority from U.S. Provisional Patent Application No. 60/080,268 filed on Apr. 1, 1998.

BACKGROUND OF THE INVENTION

The present invention relates to a system and method for electrical stimulation of the inner ear. More particularly, the present invention relates to an implantable device for electrical stimulation of the $8^{th}$ nerve. Even more particularly, the present invention relates to an implantable device for electrical stimulation of the $8^{th}$ nerve to produce the sensation of hearing.

It is well known that brain and nerve impulses are electrical in nature. It is also known that electrical stimuli applied to receptor centers such as the nerves cause a reaction dependent on the electrical characteristics of the stimuli. Many devices utilize these characteristics to compensate for defective performance of sensory organs of the body.

In normal hearing, the hair cells are a critical link in the hearing chain. They serve two functions in association with the brain: (1) they establish a background nerve activity that is perceived as silence ("active silence" as described below); and (2) when sound enters the ear, they generate a potential that varies and modulates this background nerve activity in response to the sound. The resulting nerve activity is a constant plus the derivative of the atmospheric pressure. This derivative or rate of change of pressure carries the sound information. Important to the present invention is the recognition that the rate or frequency or density of the resultant nerve activity may be viewed as a carrier modulated by sound.

In the profoundly deaf patient, the principal cause of deafness is the loss of function of the hair cells. In 30% of the deaf, the loss of nerve fibers from the spiral ganglion to the non-functioning hair cells is a contributory cause of deafness. This may be caused due to inactivity of the nerve fibers from the hair cells to the spiral ganglion. Therefore, to restore hearing to a person with a partial or total (profound) loss of hearing, a replacement of these functions is required past the point of loss of function, that is at a higher link to the brain.

In the case of the ear and associated hearing functions, many devices have been designed to electrically stimulate the auditory nerve of the human body, which is known as the 8th cranial nerve. However, these devices operate on principles derived from an inappropriate extrapolation of certain observations made by Beckesy in the 1930's. Beckesy's observations concerned the Basilar membrane, which extends the entire length of the Cochlea. These observations revealed that the Basilar membrane vibrates in response to sound vibrations that enter the ear. It was observed by Beckesy, and confirmed by others, that the sound vibrations caused the membrane to vibrate with a standing wave wherein the maximum amplitude of the standing wave occurred at a location on the membrane dependent on the frequency of the entering sound vibrations. Individual hair cell activity at these locations was also particularly pronounced at the locations of the maximum amplitude of the standing wave. High frequencies result in a maximum amplitude at the entrance to the Cochlea. As the frequency decreases, the location of this maximum amplitude moves toward the extreme end of the Cochlea.

While this mechanical action is true and individual hair cell activity is emphasized at these maximum amplitude locations, others have inappropriately extrapolated these observations to conclude that hearing was effected by the response of the individual nerve fibers along the length of the Cochlea that were frequency dependent. Thus, the theory developed, known as the Place Theory of hearing, that the nerve fibers in the Cochlea conduct different frequencies to the brain dependent on their location in the Cochlea. It is curious that the absolute length of the cochlear duct, which varies from 5 mm in the chicken to over 100 mm in the whale, does not seem to play a very important role in the frequency range of the Cochlea, i.e., the whale has a slightly greater frequency range than a chicken even though the Place Theory of hearing would suggests that, with a Cochlea that is 20 times longer, the whale's frequency range should be 20 times greater than the chicken's.

The Place Theory of hearing requires that the nerves in the Cochlea operate in a manner different from the manner in which all other nerves in the body operate. The present invention is based on a model of hearing that is entirely different than the Place Theory. This invention, in contrast to the Place Theory, is based upon the application of signal processing principles to the function of the nerve fibers of the $8^{th}$ nerve terminating in the vestibule and Cochlea, much like the operation of modern communication receivers that use Digital Signal Processing to reduce noise and process information.

The nerves terminating in the Vestibule and/or Cochlea that transfer sound sensation are non-specific and may be fired in sequence or as a sustained background nerve activity by a single pulse which, when modulated, produces the sensation of the sound of the modulation for a given period of time. Accordingly, given the principles guiding the present invention, the nerve fibers in the $8^{th}$ nerve operate in a manner identical to those throughout the body. In particular, the signal sent by the nerves is non-specific but the number of nerves firing and the rate of firing conveys information to the brain that the brain translates into sound. The number of nerve fibers firing simultaneously or at such a high repetition rate that it appears simultaneous is a function of the instantaneous sound intensity, variations of this nerve activity is perceived as sound.

The model of hearing upon which the present invention is based recognizes that many nerve fibers of the Cochlea have functions other than the conduction of sound. It is recognized that the very regular and orderly spatial arrangement of the sensory elements in the Cochlea predispose it to work on the basis of spatial principles, however, not in accordance with the Place Theory of hearing. It has been observed that stimulation of many of these fibers does not produce the sensation of sound. The brain utilizes the Cochlea as a mechanism to control the sound pressure variations as a result of the sound vibrations and thereby serve as a means of volume control.

In this mode, some of the outer hair cells of the Cochlea sense the motion of the Basilar membrane, transmit this information to the brain which in turn sends back signals to many of the hair cells in the Cochlea to control the stiffness of the Basilar membrane and thereby control the mechanical impedance at the entrance from the Vestibule to the Cochlea. This then allows for an automatic volume control (in the mechanical domain) and possibly a means of controlling the frequency response to improve intelligibility. Changing the mechanical characteristics of the Basilar membrane changes the mechanical transfer of energy to the hair cells thus effecting sensitivity and frequency response. The Cochlea may also contribute to the process of sound localization.

Audio signals of speech and music are found to have most of their energy concentrated in the lower-frequency ranges. To achieve an improvement in the signal-to-noise ratio, preemphasis (boosting the gain of a signal) of the high frequencies should be observed and a corresponding deemphasis at the detection in the brain. Consistent with this notion, Becksey published in 1960 that patterns of vibration of the Cochlear partition of cadavers for various frequencies showed a preemphasis of the high frequencies in the first 10-mm distance from the stapes. In 1974, Rhode published a graph of the input-output ratio, in decibels, for the Malleus and Basilar membrane (FIG. 21A). The graph shows an increase of 6 dB per octave (or 20 dB per decade) of the frequencies between 200 Hz and 8 kHz. Also FIG. 21B shows that a broad range of frequencies stimulates the hair cells in this area. These observations tend to support the concept of preemphasis. Observations also suggest that the outer hair cells of the Cochlea function to provide information to the brain to control volume, the dynamic range and have an effect on frequency response rather than to transmit the sensation of particular frequencies to the brain.

In addition, it is not generally known that the nerve activity that produces sound consists of the summation of the nerve activity in response to external sound or stimuli modulating a constant background nerve activity. This constant background nerve activity was described by R. Lorente De No in 1976 as follows, "In the absence of peripheral stimulation, the acoustic nuclei are the site of continuous activity maintained by the arrival of nerve impulses spontaneously initiated in the Cochlea. The activity is necessarily accompanied by circulation of impulses in chains of neurons.

Since spontaneous activity in the cochlea and in the acoustic centers is perceived by humans as silence, it must be concluded that the spontaneous activity serves to determine the background states of the various subdivisions of the acoustic nuclei, to which the deviations caused by sound are referred. In other words, what we hear is the result of those deviations from the ground states or baseline signal of the acoustic nuclei, which are caused by external sources of sound." He refers to this background state as "active silence" to which perception of sound is referred.

While others have observed this activity, none has recognized it as a carrier that is the summation of non-specific nerve activity and modulated by external stimuli. The recognition of this principle is an important element of the present invention. This recognition is consistent with the sample data-theorem developed by Hartley of Bell Labs and Nyquist in 1928 when one considers the "active silence" as a carrier frequency.

It is not necessary that the nerve activity be a sequence of single nerve fiber activity but that the nerve activity is at such a high frequency that it is beyond the range of audible sound, paring or multiples of simultaneous nerve findings may occur. Active silence can be compared to the molecular activity of a gas at a given pressure (silence) and the modulation of this activity by pressure variations due to sound.

The mechanical characteristics of the Basilar membrane at the entrance to the Cochlea (see FIGS. 21A and 21B) are such that the modulation is maximum for high frequencies and reduces at a rate of 6 dB per octave to the lower frequencies. Audio signals of speech and music are found to have most of their energy concentrated in the lower-frequency ranges. The emphasis of the high frequency components of the audio signal is introduced before the nerve activity noise is introduced, to the point where they produce a constant deviation of the background nerve activity as a function of frequency. This equalization, of the low frequency and high frequency portions of the audio spectrum, enables the signal to fully occupy the bandwidth of the neuron communication link. The spectrum of the noise introduced at the nerve summation output occupies the entire bandwidth. The noise-power spectrum at the output summation is emphasized at the higher frequencies. At the summation output of the nerve fibers the inverse function, deemphasis is introduced to the higher-frequency components, which restores the original signal-power distribution. This deemphasis process reduces the high-frequency components of the noise also and so effectively increase the signal-to-noise ratio.

This function of accentuating the high frequencies compensates for an inverse function at the far end of the nerve bundle in the brain. It is similar to accentuating the high frequencies in a FM transmitter and subsequently attenuating high frequencies at the receiver. The result is, with the Basilar membrane compensation for the brain "receiver" functions, an improved signal-to-noise ratio. A secondary characteristic of the Cochlea is that all frequencies do in fact stimulate nerve fibers near the Vestibule with preemphasis. High frequencies dominate the entrance and low frequencies dominate the other end. However, the sensing of a frequency is not related to which nerve fibers are stimulated but rather to the change in overall nerve fiber activity when looking at the summation of all nerve fiber activity (see FIG. 20)

The foregoing function of the Cochlea might be compared to a woofer, mid-range and tweeter speaker system. When the sounds arrive at the ear, an individual hears the summation of the activity of each of the speakers. Similarly, the brain receives signals that constitute the summation of the activity and signals sent by the hair cells and the associated nerve activity. Importantly, however, the nerve activity associated with each stimulated hair cell makes a contribution to the summated nerve activity entirely independent of the contribution made by the nerve activity of other stimulated hair cells but is effected by other nerve activity. Thus, oftentimes, when observed in isolation, the nerve activity seemed to be frequency selective. However, when looked at closer in light of the recognition of the spontaneous or background activity of the hair cells as a carrier frequency for sound stimuli received, the recognition of the present invention that the modulation of background or spontaneous nerve activity is what is "heard", not the nerve activity associated with individual hair cells, becomes apparent.

While it is true that different frequencies may increase activity of nerve fibers in different areas of the Cochlea, this does not effect the transmission of sound. The summed change in nerve activity from the Vestibule and the Cochlea is heard as sound, not which nerve fiber is activated at any time or when a given frequency is heard. This concept was first suggested by Rinne in 1865 but he had no formal theory to put forward. In 1880 Rutherford provided a plausible explanation, the TELEPHONE THEORY. However at that time little was known of nerve fiber characteristics and it would be almost 50 years before Hartley's and Nyquist's SAMPLE DATA THEOREM.

The physiological characteristics of the $8^{th}$ auditory nerve are likewise important in designing any system based on the theory of hearing adopted above. In particular, five characteristics play an important role in the design of any such system: strength-duration, streaming, latency, recovery, and fatigue. The strength-duration characteristics of the human nerve fibers are graphically represented by the strength-duration curve shown in FIG. 1A. The strength duration curve expresses the relation between least strength of an applied current (stimulus) to the nerve fiber and the least time during which the current (stimulus) must flow to reach a threshold for excitation. Expressed another way, the strength-duration curve is a plot of the threshold intensity just capable of exciting an axon and its relationship to the duration of the stimulus current. Indeed, nerve fibers will not excite in response to current densities below a minimum. The strength-duration curve is further described in *Medical Physiology and Biophysics*, Ruch and Fulton, 18th Edition, W. B. Saunders & Co. Ruch and Fulton model this nerve behavior after a single resistance capacitance circuit. Strength duration combined with a gradient electric field determines the range of pulse length for a stimulus pulse to cause "streaming."

Streaming is the sequential firing of nerve fibers within a group of nerve fibers or ganglia that have been stimulated by a single-pulse stimulus. Upon stimulation by a single-pulse stimulus such as a single square wave through action of a gradient electrical field impinging on a group of nerve fibers or ganglia, the individual nerve fibers within the group will each receive a stimulus decreasing in intensity as the individual nerve fibers within the group increase in distance from the source electrode. This phenomenon is shown in FIG. 1B. The firing rate of the individual nerve fiber will correspond to that shown in the strength-duration curve of FIG. 1A. Thus, when the individual nerve fibers within a stimulated nerve group commence firing, those closer to the origin of the gradient field will fire at a greater rate while those farther away will fire at a slower rate.

Thus, the nerve group will transmit a series of signals, i.e., a stream of nerve activity, over time. In particular, this "streaming" is characterized in that some nerves in the group will fire in succession, which successive firings occurring at a slower rate than the previous firing.

Streaming occurs during the latter portion of a single nerve pulse stimulus. The length of streaming of a group of nerve fibers is limited by the delay of the start of streaming at the beginning of the pulse (no sooner than 0.1 milliseconds according to the strength-duration curve of FIG. 1A) and the time remaining to the end of the stimulus pulse. This behavior is shown at the top portion of the graph of FIG. 1A by the line labeled as the "Nerve Firing Rate." The latency period is the delay between the start of the stimulus pulse and the firing of a nerve fiber.

Reference to FIG. 1A shows that the latency time For each nerve fiber is different as defined by the strength-duration curve and the gradient field. In practice it is desirable to have the starting of streaming to be delayed by more than 0.2 ms. As the latency time is shortened by increasing the stimulus amplitude, the compensation component necessary to keep the differential latency times constant during streaming requires increases the stimulus to an excessive amplitude for a system with a long streaming time, gas in the 4 channel system). The minimum latency period also determines the overlay time for adjacent channels i.e., the time in which the adjacent or other nerve fibers must be stimulated to continue the transmission of the total signal once the original nerve fiber channel enters the recovery stage.

Moreover, the $8^{th}$ nerve individual fibers are not capable of indefinitely transmitting stimuli. After receiving and transmitting a stimulus, the nerve must go through a recovery period. Absent this, the nerve will fatigue and will cease transmitting. The recovery characteristics of the nerve limit the repetition rate of individual channel stimulation. Lastly nerves are damaged by prolonged stimulus with an average DC component. All such stimuli must be made in an AC fashion.

When an electrical field impinges on the auditory sensory branch of the $8^{th}$ nerve including the brain stem or the spiral ganglion, the angle of arrival produces a gradient field across the nerve group that can causes the nerves to fire in sequence. This is illustrated in FIG. 1C, which indicates how the strength of an electric field decreases across a group of nerve fibers, between a cathode and an anode. Because of this decreasing strength electric field, the nerve fibers fire in sequence. In addition, because of the combination of the electric field and the strength-duration characteristics of the nerve fibers, as the distance from the cathode increase, the time between successive nerve firings also increases. In contrast, with the arrangement shown in FIG. 1D, all of the nerve fibers are subject to substantially the same electric potential and will thus fire substantially simultaneously.

If the stimulus amplitude is small, so as not to produce a high enough carrier frequency to be above the range of hearing the streaming frequency can be heard. Its frequency is a function of the stimulus place on the strength-duration curve in relation to the nerve fibers stimulated and the curve's slope. This varies with time and amplitude of the stimulus. As mentioned above, the signal sent by the nerves is non-specific but the number of nerves firing and the rate of firing conveys information to the brain that the brain translates into sound. For example, as the amplitude is increased, the rate of sequential nerve fiber firing increases. If the angle of a stimulus is near perpendicular a high rate of sequential firing will occur as the individual nerve fibers of a channel receive close to the same stimulation. If the angle is small the sequential firing is at a lower frequency as the difference of stimulation across the individual nerve fibers stimulated will have a greater range.

Known devices which are designed to aid the profoundly deaf by electrical stimulation of the $8^{th}$ nerve but on principles guided by the Place Theory, however, function primarily because of this angle and stimulus dependency, but with results that are not predictable, repeatable or optimized. In U.S. Pat. No. 3,449,768, issued to James Doyle, the system was not designed based on principles of the Place Theory of hearing but was designed to produce a carrier of nerve activity based on multiple channels stimulated in sequence at a rate sufficiently high to result in a carrier of nerve activity suitable for modulation with sound information. That patent discloses a device for applying electrical stimuli to the $8^{th}$ cranial nerve and includes an electrode system for placement in the vicinity of the auditory nerve, means for feeding pulses to a plurality of transmission channels and a modulator which modulates a time-amplitude integral of each of the pulses.

This system was limited because, for example, of the number of channels required and the recovery time allowed for each channel was too short to allow for prolonged stimulus without causing nerve fatigue. No consideration was given to the latency characteristics of nerve fibers (the delay between the start of the stimulus pulse and the firing of a nerve fiber). Moreover, the earlier Doyle system failed to allow for compensation in the stimulus strength to maintain a constant nerve firing rate and overcome the inherent slowing due to streaming, as described above. Lastly, the earlier Doyle patent did not recognize or teach that the carrier frequency (the frequency or density of the background nerve activity) is independent of the rate at which the individual channels are being fired and the number of the individual channels. These limitations or failures resulted in a system with low sound fidelity, a signal to noise ratio that is lower than can be achieved otherwise, and a constant hum or tone perceived by the patient.

SUMMARY OF THE INVENTION

An object of this invention is to improve systems for stimulating the auditory nerve of the human body.

Another object of the present invention is to improve the system disclosed in U.S. Pat. No. 3,449,768, issued to James Doyle.

A further object of this invention is to produce continuous nerve activity mimicking the spontaneous nerve activity present in normal hearing and to modulate this nerve activity with an audio signal to provide hearing.

A further object of this invention is to provide a new system for stimulating groups or bundles of nerve fibers of the 8th cranial nerve in a manner to cause channel streaming at a constant rate.

Still another object of the present invention is to accomplish this constant rate streaming in a manner that accounts for the strength-duration characteristics of the nerves.

Another object of this invention is to modulate this channel streaming with audio information to produce hearing for the profoundly deaf or those with other hearing impediments.

The present invention provides a new system for stimulating groups or bundles of nerve fibers of the $8^{th}$ cranial nerve in a manner to cause channel streaming at a constant rate. With the preferred embodiment of the invention disclosed herein in detail, unlike any prior art device, this constant rate streaming is accomplished in a manner that accounts for the strength-duration characteristics of the nerves. Further, the system modulates this channel streaming with audio information to produce hearing for the profoundly deaf or those with other hearing impediments. The present invention provides further a method for stimulating these groups or bundles of nerve fibers.

In accordance with the preferred embodiment of this invention, an electrical stimulus is applied so as to cause nerve firing at a constant rate. The increase in stimulus strength provided by the device of the present invention is governed by the strength-duration characteristics or behavior of the nerve fibers or ganglia. By adjusting the gradient field generated by the electrodes placed in proximity to the $8^{th}$ nerve or the nerve characteristics represented by the strength-duration curve, the individual nerve fibers located within the gradient field need not fire simultaneously when stimulated, as taught in the prior art, but will fire in a sequence of nerve activity as time progresses.

Preferably, the stimulus does not occur at the extremes of the strength-duration curve. This is because the high voltage needed to obtain a very short latency period may produce undesirable electromechanical reactions. Also, a long latency period results in an excessive channel overlap and reduces the available time per channel for streaming. For instance, preferably, the latency period is kept between 0.1 and 4.0 milliseconds; and even more preferably, the latency period may be maintained between 2 and 3 milliseconds. It should be noted that the preferred latency period may vary depending on the specific subject or patient, and, with some individuals it may be appropriate or preferred to operate outside of the above-described ranges.

While this streaming of nerve activity takes place, the device of the present invention modulates the stimulus pulse to vary the nerve activity rate and cause the transmission of signals to the brain by the $8^{th}$ nerve or the ganglia that are perceived as hearing. It also modulates the combined stimulus pulse and its audio modulation to cause the streaming to remain constant when no sound is present. It follows therefore that as the amplitude of the stimulus pulse increases, the percentage of modulation due to sound remains constant. In other words as the stimulus amplitude increases so also does the audio modulation component.

In embodiments of the present invention in which more than one channel is employed, adjacent channels overlap, due to the latency and recovery characteristics of the nerve. This is done so that a constant stream of summated channels is transmitted. The device of the present invention therefore provides a constant stream of nerve activity independent of audio modulation that acts as a carrier wave but that will not be perceived by the brain as sound but merely as "active silence" as the term is understood in the art. In addition to stimulating the nerves fibers in such a way as to create a carrier wave, the present invention further utilizes this carrier wave to cause the sensation of sound by modulating it at appropriate times during the stimulus signal duration and the nerve fibers' response.

Devices made in accordance with the teachings of the present invention contain a means of generating a background nerve activity, perceived by the brain as silence. Such devices utilize this background nerve activity as a carrier of audio information and modulate this nerve activity with audio information. This modulation causes a variation of the density of the background nerve activity which is perceived by the brain as sound. Importantly, however, such modulation is accomplished in a manner such that the frequency or density of the background nerve activity is independent of the number of electrical channels used by the device (so long as the number is greater than one) and the rate at which any given channel is being stimulated. Thus, the rate at which any stimulus is applied to any channel, and the duration of any pulse, is secondary in function to the main objects of this invention. Indeed, the summated nerve carrier frequency may then be produced at greater than 1000 cycles per second, which exceeds the recovery time for a single nerve fiber, and independent of the modulating frequency.

A method is disclosed for causing a stream of nerve fiber activity resulting in a background state of nerve activity on the audio transmission branch of the $8^{th}$ nerve to flow to the brain and modulation of this stream (pseudo carrier) with audio information. A device is described for stimulating the auditory transmission branch of the $8^{th}$ nerve. It uses electrodes designed to restrict the electrical field to the region of their respective nerve fiber group and to produce a gradient field for each channel such that the latency characteristics of the nerve fibers in a given channel will cause a sequential firing (streaming) of the nerve fibers during a portion of the channel stimulus pulse. In the analog system the nerve fiber channels are stimulated in sequence but with their stimulus overlapping their previous channel by an amount equal to the shortest latency period of the channel.

During the period when a stimulus pulse is causing nerve fiber streaming, the pulse amplitude is modulated with the audio information. In addition during the nerve fiber streaming either electrical means or the shape of the probe or both compensate, through the strength of the stimulus, for the Strength-duration characteristics of the individual nerve fibers such that when no sound is present the streaming rate is substantially constant resulting in "active silence", i.e., a minimum of sound sensation.

Thus, the stimulus pulse is divided into two periods. In the first period, the nerves, to which the pulse is applied, do not fire. All of the firings of the nerves occur in the second period of the stimulus pulse. It may be noted that these two periods, typically, are not equal in length; and in fact, with the specific examples disclosed herein in detail, the second period is substantially longer than the first period. The desired streaming—that is, sustained nerve activity and at a uniform rate—can be caused by changing the stimulus pulse during the second period or both the first and second period. The audio modulation of the streaming, however, is done only in the second period of the stimulus pulse.

In the digital system, there is no streaming as there is a single firing time for nerve fibers in a channel. The channel overlap exists over a number of channels and the audio modulation is in the form of frequency modulation of the streaming frequency and independent of the channel sequence frequency.

An aspect of the present invention involves producing or enhancing a carrier of background nerve activity that is perceived as silence and modulating the background nerve activity (a pseudo carrier) to produce the sensation of sound and to restore a degree of hearing when the organ of sound is totally defective.

Another aspect of the preferred embodiment of this invention involves a system which transforms sound into a corresponding electrical signal and includes a coding device for converting the analog signal into a pulse train of nerve stimulus applied to at least 2 groups of nerve channels simultaneously. Further, the preferred system includes a transmitter coupler, a receiving coupler, and a multi-channel gradient probe for impressing electrical stimulus to a nerve bundle and means for independently adjusting each channel stimulus amplitude.

A further aspect of the preferred embodiment of the present invention involves an electrode system within the Vestibule and/or Cochlea for stimulating individual nerve fibers of the auditory nerve therein, generating nerve fiber activity which is transmitted to the brain in a simple pulse pattern, whereby a background nerve activity (pseudo carrier) is modulated by the audio information, whereby the modulation of the density of the background nerve activity is perceived as sound. See FIG. 20.

An additional aspect of the present invention involves generating a nerve activity carrier frequency not dependent on the number of stimulus channels and allowing time for the activated nerve fibers sufficiently to recover so that no fatigue will occur on the stimulated nerve fibers.

A further aspect of the present invention involves a means for stimulation of any number (N) of different fiber groups or portions of the Spiral Ganglion of the sensory branch of the $8^{th}$ nerve, phased in N spaced time intervals with a portion of each adjacent group overlapping. The time interval between the repetitions of any group stimulus is substantially longer than the natural recovery time of a single nerve fiber or portion of the Spiral Ganglion after electrical stimulation. Five milliseconds are chosen in the preferred embodiments to avoid fatigue of the nerve group after an applied stimulus. This represents about 5 time constants of the recovery time of a nerve, leaving a residue of about 1% from pervious stimulus.

An advantage of the present invention is that sufficient recovery time for nerve fibers to recover from previous stimulus is allowed so as not to fatigue the nerve fibers. A further advantage is that the present invention provides a continuous stream of nerve fiber activity not directly related to the channel repetition rate thereby avoiding the limitations of the system disclosed in U.S. Pat. No. 3,449,768 which required a channel rate dictated by sample data theory criteria.

Advantageously, the power required for nerve stimulus is reduced due to the proximity of the stimulus electrodes to the nerves in the audio transmission branch of the $8^{th}$ nerve. Potentials less than one volt are sufficient to trigger a nerve fiber without causing electrochemical reactions of the metal/tissue.

The use of one-cycle stimulus pulses having an average DC value of 0 reduces the possibility of electrochemical reactions of the metal/tissue. Hereinafter, the term "biphasic" is used to refer to a stimulus pulse having an average DC value of 0. U.S. Pat. No. 5,674,264 mentions that manufacturers of cochlear implant systems have to be careful to control electrode voltages to keep them in a region where any electrochemical reactions occur at a rate too slow to cause damage. Advantageously, the embodiments of the present invention effectively eliminate these reactions.

There are two limits on the use of the strength-duration curve. If the latency period is too short, the amplitude of the stimulus will be high, but more important the compensation to keep the streaming constant for an extended period of time will require a very high stimulus. This can put the electrodes in jeopardy of causing electrochemical reactions. As the number of channels is increased this effect is less pronounced.

The present invention ensures a constant background nerve activity during a single nerve fiber's streaming. The present invention accomplishes this by canceling out the nonlinear characteristics of the nerve fiber's streaming, as represented by the time constant of the strength-duration curve. Such cancellation may be accomplished by one or both of the following techniques: (a) modulating the stimulus pulse with a similarly canceling time constant; or (b) causing the gradient field emanating from the electrode to be shaped in such a manner as to cancel the strength-duration curve.

The embodiments of the present invention provide normal sensations of sound to the recipient. For those who have heard in the past no extensive training is required to interpret sound.

The present invention will also produce sound sensation for those whose hair cells and nerve cells have been destroyed. Oftentimes, the cause of deafness or defective hearing is due to the destruction of hair cells in the ear. In such circumstances, the stimulation of the nerves in the manner described herein will produce the sensation of sound. However, in some circumstances, the nerves going to the hair cells in the ear of profoundly deaf patients or patients with defective a hearing are also destroyed. In such instances, the present invention will produce sound sensations by electrically stimulating the Spiral Ganglion in the manner provided for herein or stimulating at a higher level as at the brain stem.

In summary, the present invention produces continuous nerve activity mimicking the spontaneous nerve activity present in normal hearing and modulates this nerve activity with an audio signal to provide hearing.

BRIEF DESCRIPTION OF THE DRAWINGS

FIG. 1A also shows the logarithmic nerve firing rate or streaming;

FIG. 7 is one configuration of a multi-channel gradient probe of 16-channels.

FIG. 15A is a drawing of the 4-channel probe using electrodes perpendicular to the probe and an enlarged ground-plain.

FIG. 16 is a block diagram of the digital system.

DETAILED DESCRIPTION OF THE PREFERRED EMBODIMENT

The nerve fibers in the $8^{th}$ nerve that transmit audio information to the brain are divided into N separate sections. Each section consists of a number of nerve fibers or portions of the Spiral Ganglion. Each section is independently stimulated by an electric pulse, which is divided into two time periods. During the first period, the stimulus amplitude of each section is held at a constant such that the first nerve fibers activated have a latency period substantially equal in time to the other sections. During the second period, the pulse amplitude will vary in a manner to cause some of the remaining nerve fibers in that section to be activated at a constant rate to the end of the stimulus pulse. This compensation may also occur during the first period as it remains fixed and contains no audio component. During the second period the audio modulation is superimposed varying the nerve-firing rate.

If the compensation of the pulse amplitude includes the first period, it is still important to recognize that the audio modulation is superimposed only in the second period, i.e., when streaming in the group nerve fibers is occurring. The sections are stimulated in a cyclic manner. Section N+1 stimulation starts at a time such that its 2nd period starts at the end of section N's stimulus pulse. During the 2nd period of each channel stimulus pulse, audio information modulates the stimulus-pulse. Since the 2nd period of consecutive channels occurs with no time gap between them, the flow of audio modulation information is continuous. The electrical probe used to stimulate a section of nerve fibers is configured so that the stimulation amplitude is different for different nerve fibers in that section. This causes the latency periods to be different for different nerve fibers thereby causing the nerve fibers to fire sequentially during the 2nd period.

Figure 1A:
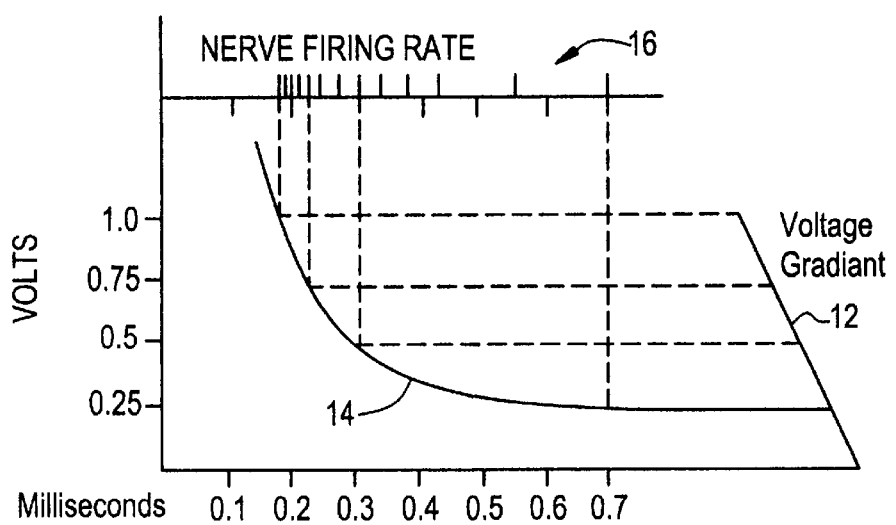
FIG. 1A is a graph of the strength-duration curve and illustrates a gradient electrical field imposed on a linear matrix of nerve fiber endings and the effect of the Strength Duration characteristics of a nerve on the time when each nerve fiber is fired in relation to the strength of the stimulus received.

FIG. 1A shows a graph illustrating a gradient electrical field 12 imposed on a linear matrix of nerve fiber endings. The graph illustrates a strength duration curve 14 in (relative) volts per milliseconds. The strength-duration curve is a plot of the threshold intensity just capable of exciting an axon and its relationship to the duration of the stimulus current. The strength duration curve expresses the relation between least strength of an applied current and least time during which the current must flow in order to reach a threshold for excitation. There is a minimal current density below which excitation does not occur. The strength duration curve does not show the effects of subthreshold stimulus upon excitability. The subthreshold current flow may advantageously be used in a preferred embodiment of the present invention as a means of adjacent channel overlapping or to enhance the background state of nerve activity.

FIG. 1A further shows at 16 a firing sequence of a group of nerve fibers when a stimulus pulse is applied which has a potential gradient that causes the stimulus amplitude at each nerve fiber to be different than its adjacent nerve fibers.

Figure 1B:
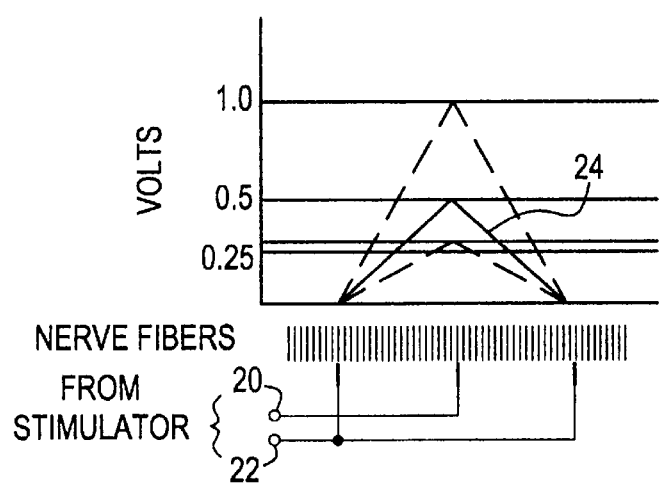
FIG. 1B shows a graph illustrating in two C dimensions one channel of a gradient probe and the gradient field impinging on the nerve endings in the proximity of the probe.
Figure 1C:
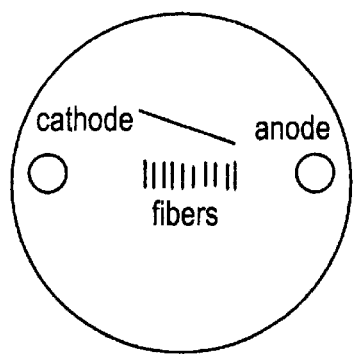
FIGS. 1C and 1D illustrate electric fields at two different angles relative to a group of nerve fibers.
Figure 1D:
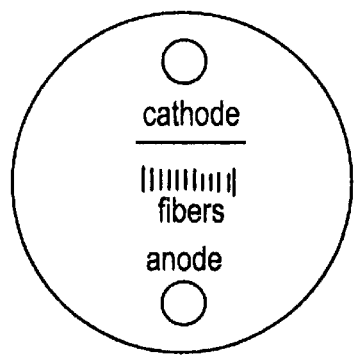

FIG. 1B shows a two dimensional graph illustrating one channel of a gradient probe and the gradient field. FIG. 1B shows the location of the active and ground electrodes 20 and 22 for a single stimulus channel. The active electrode and each of its' associated ground electrodes produce a gradient field between the electrodes and for a small distance above the electrodes. The gradient probe is placed such that the nerves to be stimulated are in this gradient field either between the electrodes or immediately adjacent to the electrodes. FIG. 1B also shows the gradient field 24 in terms of a voltage. The illustrated range for the voltage is exemplary and does not represent actual voltages used. Those skilled in the art will appreciate that nerve fibers can be stimulated with as low as 100 millivolts.

16 CHANNEL STIMULATOR CIRCUIT

A 16-channel system using a 200 Hz repetition rate produces a channel-switching frequency of 3,200 Hz. It requires an average of 7.5 nerve fibers streaming per channel to achieve a 24 kHz neuron-carrier frequency. Amplitude modulation of the pulse stimulus (to provide the sensation of sound) is transformed into frequency modulation of the neuron-carrier frequency. Precision in tracking the strength-duration curve is not required as only a small portion of the strength-duration curve is utilized. With this number of channels, the streaming time per channel is only 0.25 ms and the variation of slope during that time is small.

Figure 2:
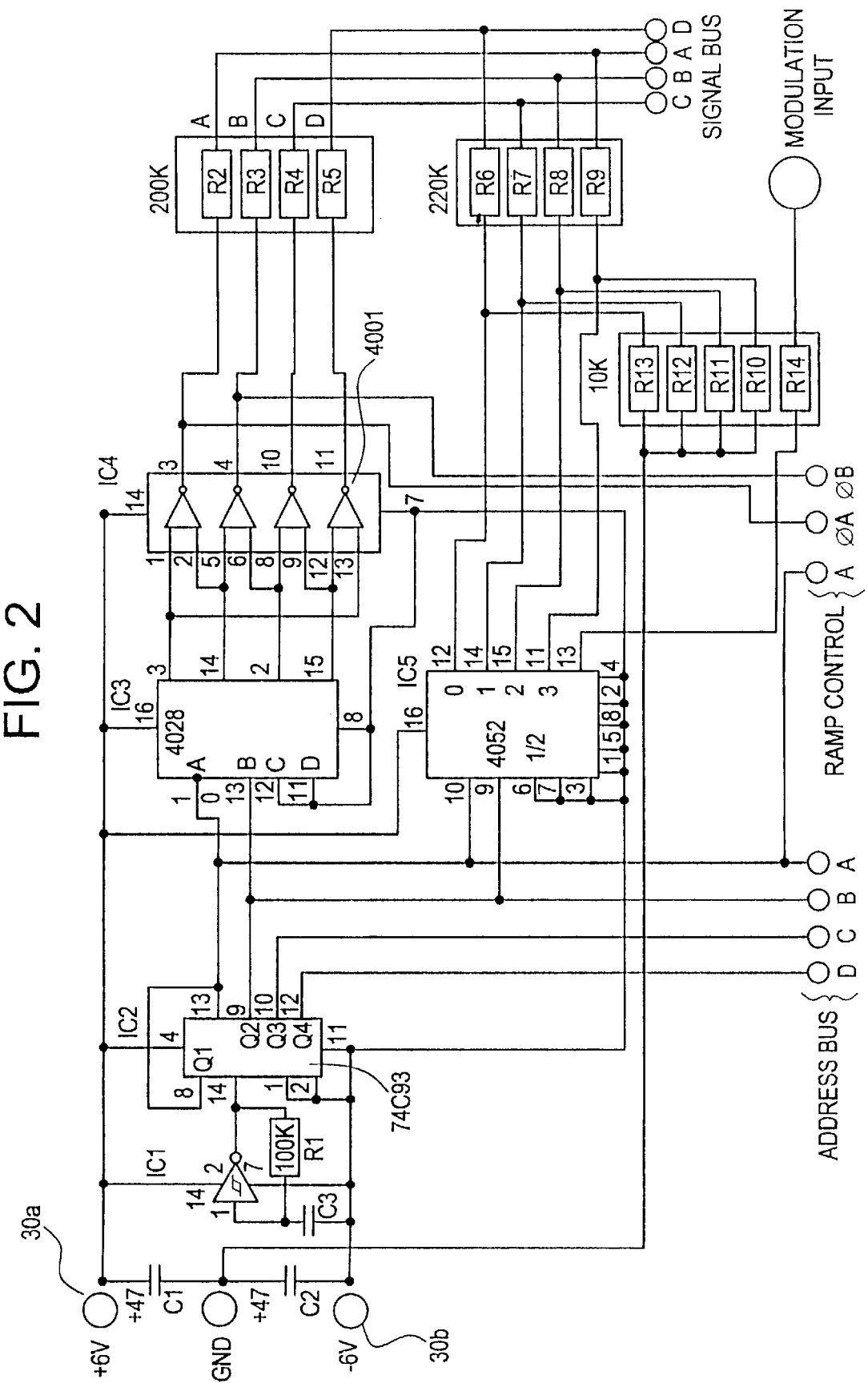
FIG. 2 is the schematic of the clock, modulator & four-phase signal generator for a 16-channel system.

FIG. 2 is the schematic of the clock, modulator and signal generator. Its function is to generate a sequence of bi-phasic pulses and the appropriate modulation of a portion of the bi-phasic pulses.

Starting at the left of FIG. 2 are the terminals 30a and 30b for the power source of +6 volts and −6 volts. Across both the + and − terminals are filter capacitors C1 and C2 to provide stable voltages free of shifts due to variations in current requirements. The Schmitt trigger ICI (⅙ of a 74C14) along with R1 and C3 form an oscillator, which provides the clock of the system. The values of R1 and C3 determine the clock frequency. The output of the Schmitt trigger drives IC2 a 4 bit binary counter (74C93). This counter divides the clock signal by 16.

The two least significant digits of the output of the counter IC2 drive the least significant inputs of a 4028 BCD to Decimal Decoder IC3. The 2 most significant inputs are grounded making the 4028 in effect a 2 digit Binary Decoder. The four outputs representing logic values 0 through 3 (4 separate states) drive the 4001 Quad 2-Input NOR Gates IC4. The 4 outputs of the NOR Gates are bi-phasic signals that swing between the power supplies rails of +6V & −6V and are shifted in phase from each other by 90 degrees (see FIG. 2). These outputs drive 220K resistors R 2, 3, 4. &5. These outputs will be summed with the modulation signal.

At the bottom right of FIG. 2, the modulation input goes through a 10K resistor R14 to the input one half of a 4052 dual 4-Channel Analog Multiplexer IC5. The channel selection inputs of IC5 are in parallel with the inputs of the 4028 IC3. The outputs of ICS are modulation signals delayed by 90 degrees from the outputs of IC4. The outputs of IC5 drive 220K resistors R 6, 7, 8, &9 which sum with the outputs of R 2, 3, 4, & 5. The timing causes the modulation to only be imposed on the last half components of the bi-phasic pulses. R14 is a resistor in series with the modulation signal. It provides a 10K input resistance to IC5 from the modulation source.

The outputs of the 4052 also go through resistors R 10, 11, 12, &13 to electrical ground. Their function including R14 is to keep the impedance substantially constant on the input to resistors R 6, 7, 8, & 9 so that the value of the summed outputs remains substantially independent of which channel ICS has selected. There are three outputs from this circuit. At the bottom left is the 4-digit ADDRESS BUS that is driven by the outputs of IC2. At the right is the SIGNAL BUS containing the 4 phase shifted bi-phasic analog stimulus signals including their modulation, and at the bottom center is the ramp control signals. At the bottom right of center are the RAMP CONTROL outputs.

Figure 3:
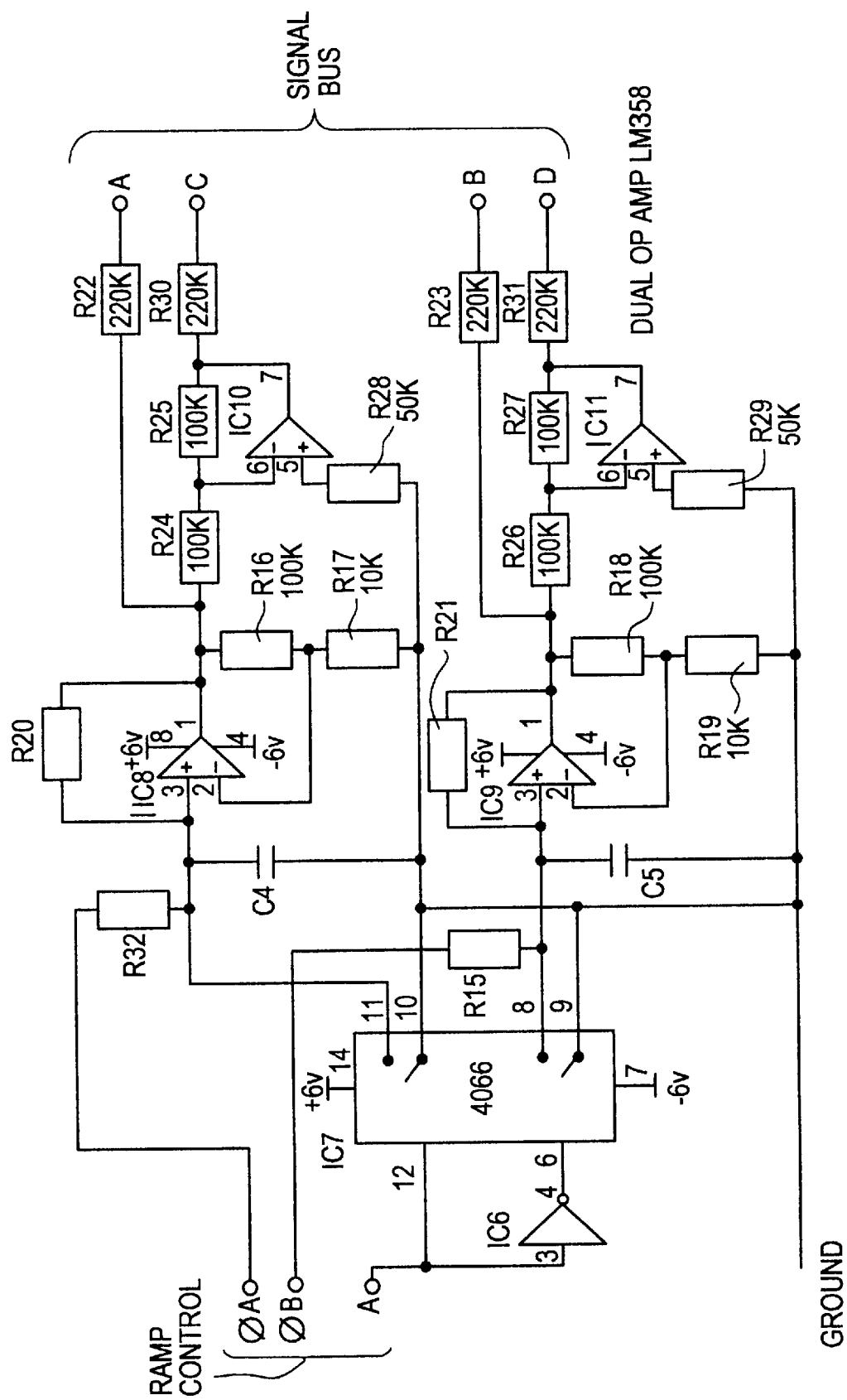
FIG. 3 is the schematic of the ramp generator for a 16-channel system.

FIG. 3 is the schematic of the ramp generator. At the left of the figure are the three control signals that come from the ramp control of FIG. 2. The A line drives a control line of a Bilateral Switch 4066, IC7 and through an inverter IC6 to a second control line of IC7. The phase A and phase B signals coming from FIG. 2 charge capacitors C4 and C5 through resistors R32 and R15. When IC7 switches are open, a voltage ramp occurs. IC8 and IC9 are operational amplifiers each having a positive gain of 11 due to the negative feedback through resistor networks R16 & R17 and R18 & R19. Resistors R20 and R21 introduce positive feedback causing the ramp on C4 or C5 to produce at the output of the amplifiers a curved up ramp similar to the curve of the strength duration curve. R22 and R23 sum these ramp output signals from IC8 and IC9 on to the SIGNAL BUS with the A and B signals from FIG. 3. IC10 and IC11 are operational amplifiers connected with a gain of −1. The resistors R24 & R25 and R26 & R27 determine this. Resistors R28 and R29 reduce DC drift by keeping the two inputs of each amplifier at the same impedance. R30 and R31 sum the outputs of IC10 and IC11 to the SIGNAL BUS lines C and D. Resistors R22 and R23 sum the outputs of IC8 and IC9 to the A & B lines of the SIGNAL BUS.

Figure 4A:
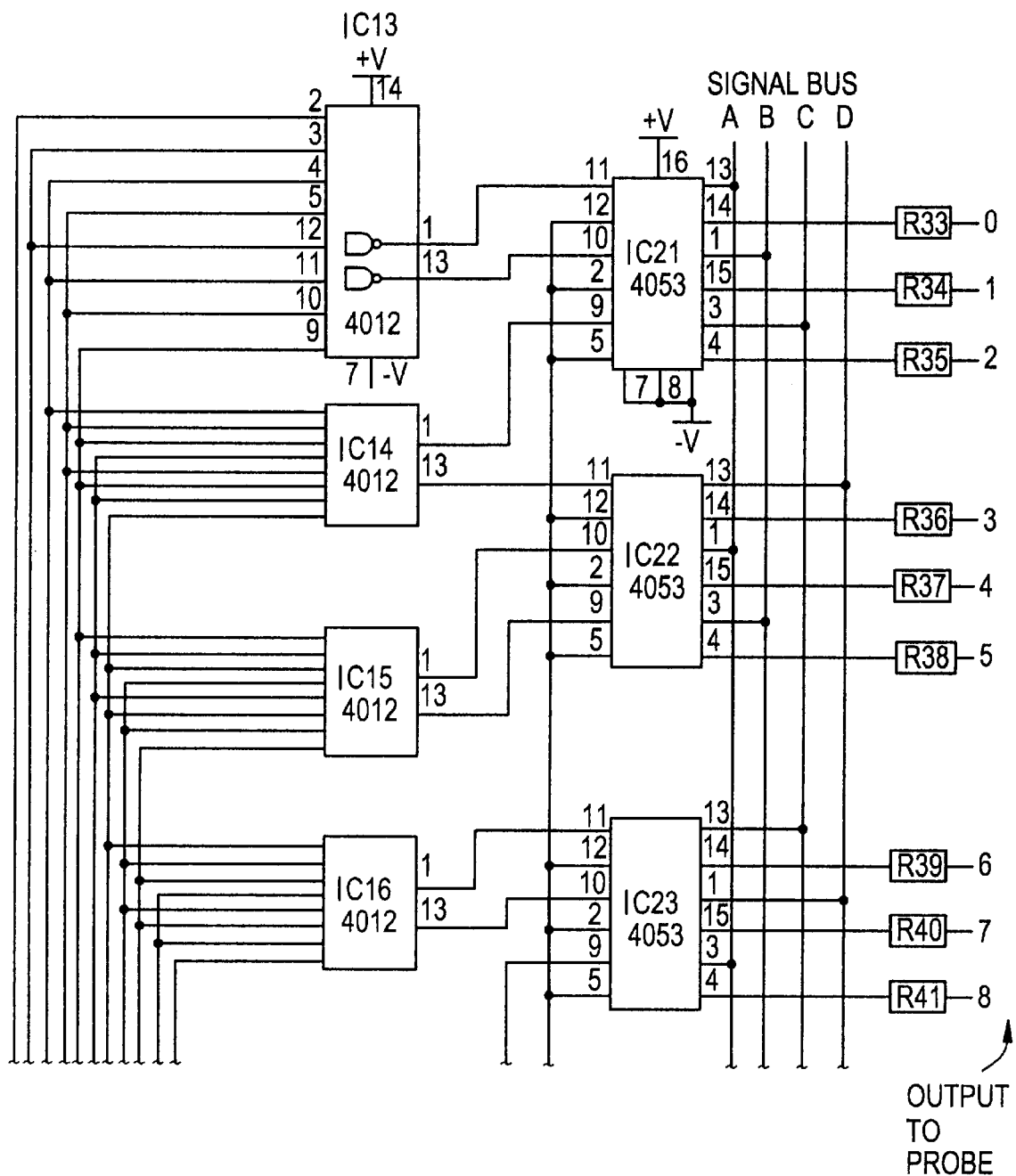
FIG. 4 is the schematic of the 16-channel multiplexer.
Figure 4B:
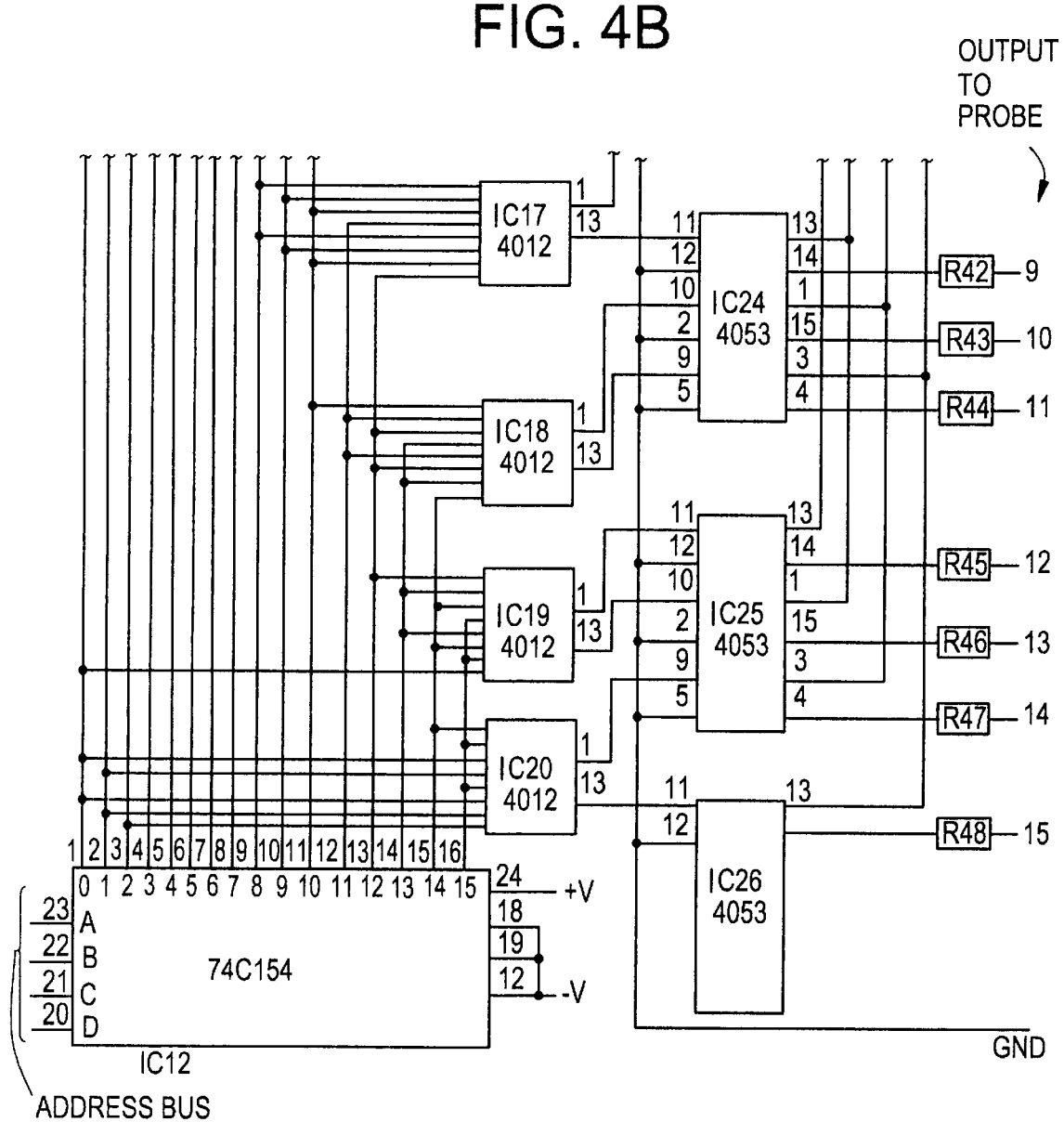

FIG. 4 is the 16 Channel Multiplexer. The ADDRESS BUS lines from FIG. 2 connect to the address bus input at the bottom left of the figure. The ADDRESS BUS drives the address input lines of IC12, a 74C154 4-line to 16-line Decoder. The output of the Decoder IC12 has 16 lines (0 through 15) that turn on one at a time in sequence in a cyclic manner. The first 4 lines 0 through 3 go to the input of a 4-input NAND Gate IC13A (½ of a 4012 Dual 4-Input NAND Gate IC13). The output of the IC13A NAND Gate is high through the first 4 positions of the 16-line decoder. In a similar manner the lines 1 through 4 of IC12 go the inputs of the IC13B NAND. Its output will be delayed by one count from IC13A and so through the eight 4012 ICs IC13 through IC20. Note that this is done in a cyclic manner so that the output of the gate IC20B starts one clock pulse before the output of IC13A. These outputs which last 4 clock pulses long and are overlapped by three clock pulses from its adjacent channel control Triple 2-Channel Analog Multiplexers ICs 21A, B, C through IC26A.

The multiplexer when on selects the bi-phasic Signal A to connect to its output when turned on and signal ground when turned off. In a similar manner IC21B switches Signal B, IC21C switches Signal C, IC22A switches Signal D, IC24B switches Signal A and so forth through IC26A and then back to IC21A. When the switches are not connected to one of the Signal A, B, C, D lines they are grounded to prevent crosstalk and prevent leakage currents. The outputs of the Multiplexer switches are of low impedance and provide a voltage output. Resistors R33 through R48 change the voltage output into a current to drive the nerve probe. Their resistance value is substantially higher than the resistance of the nerve probe electrodes thereby insuring that the nerve drive is relatively independent of the probe resistance path to the nerves.

Fine adjustment of output current can be done by varying the power supply voltage which has a small effect on the clock frequency or by placing a shunt variable resistors across each Signal line A, B, C, &D to signal ground which will reduce the voltage swing of these points and therefore reduce the current drive to the nerve. Each variable resistor effects only ¼ of the 16 outputs, therefore the 4 variable resistors are ganged.

Figure 5:
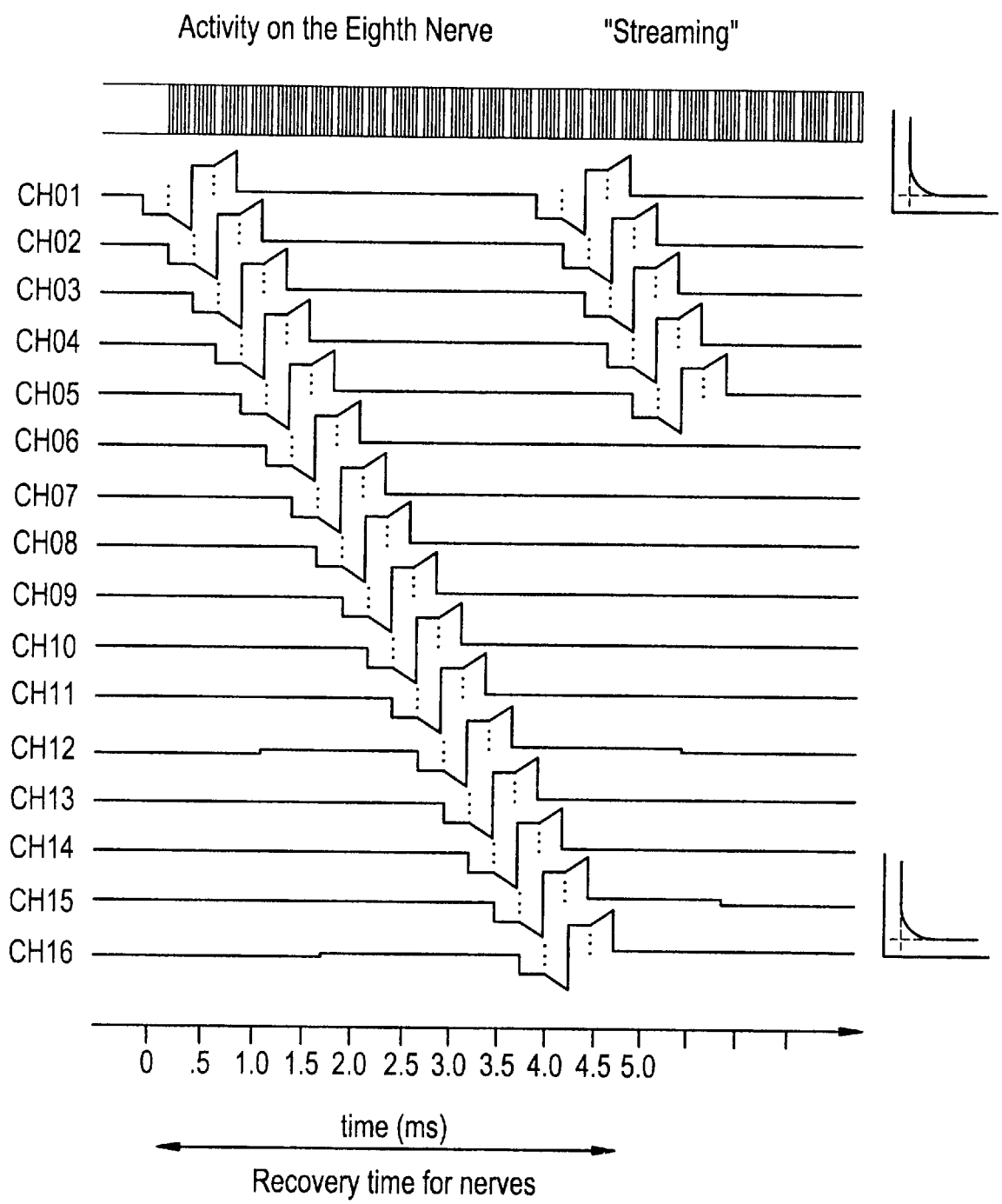
FIG. 5 is a chart showing the timing relationship between the 16 channels, the electrical waveforms including the Strength Duration compensation and the continuous nerve activity on the auditory branch of the $8^{th}$ nerve.

FIG. 5 shows the waveforms of the 16 channels. As shown in the figure, each channel is delayed by 90 degrees of a complete pulse cycle. The amplitude of the stimulus pulse is set so that nerve streaming (or firing) starts at the start of the slope compensation. Note that the slope compensation may occur at the beginning of the stimulus pulse (not shown in FIG. 5) or in the second portion of the stimulus pulse (as shown in FIG. 5. However, the modulation does not occur until nerve streaming is in place.

Figure 6A:
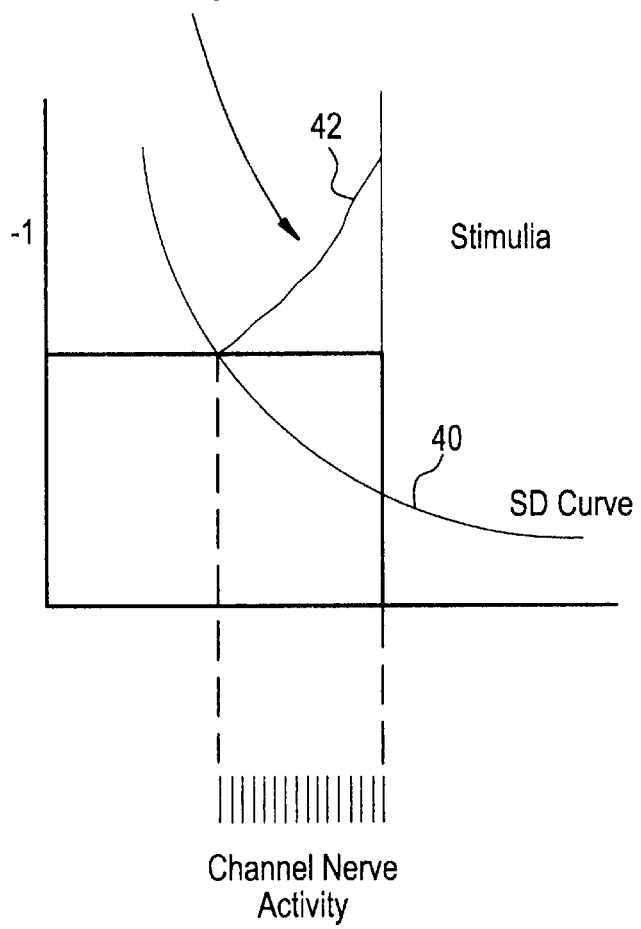
FIG. 6A is a chart showing the increase in stimulus strength to compensate for the strength-duration characteristics of a nerve to produce a constant rate of nerve activity.
Figure 6B:
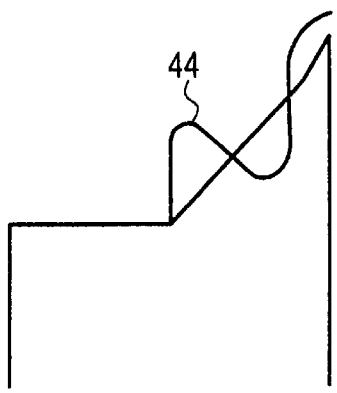
FIG. 6B shows the audio modulation imposed on the last portion of the stimulus pulse.

FIG. 6A shows the strength-duration curve 40 with the stimulus pulse 42 crossing the strength-duration curve and the compensation added to the stimulus pulse to generate a constant rate of firing of the nerve fibers. FIG. 6B shows the audio modulation 44 superimposed on the last portion of the stimulus pulse. Both figures show the stimulus in a positive direction. This is only for simplicity and does not necessarily indicate the polarity of the stimulus pulse.

FIG. 7 is a drawing of a 16-channel probe. This is connected to the channel outputs of FIG. 4. FIG. 15A shows a 4-channel probe. Its design is typical of 4-channels of a 16-channel probe.

4 CHANNEL STIMULATOR CIRCUIT

The 4-channel analog system is a configuration with the preferred minimum number of channels. Therefore it requires a preferred maximum number of streaming nerve fibers to be stimulated per channel and a preferred maximum of compensation for the strength-duration characteristics of the nerves. To achieve a 24 kHz neuron-carrier or streaming frequency let us assume a repetition rate of 200 pulses per second times 4 channels results in a total of 800 channel stimulus pulses per second. If 30 nerve fibers are activated in uniform sequence per channel, a 24 kHz neuron-carrier frequency will result. Amplitude modulation of the pulse (to provide audio sensations) then in effect transforms into a frequency modulation of the neuron-carrier frequency (more or less than 30 nerve fibers being fired per pulse).

Figure 8:
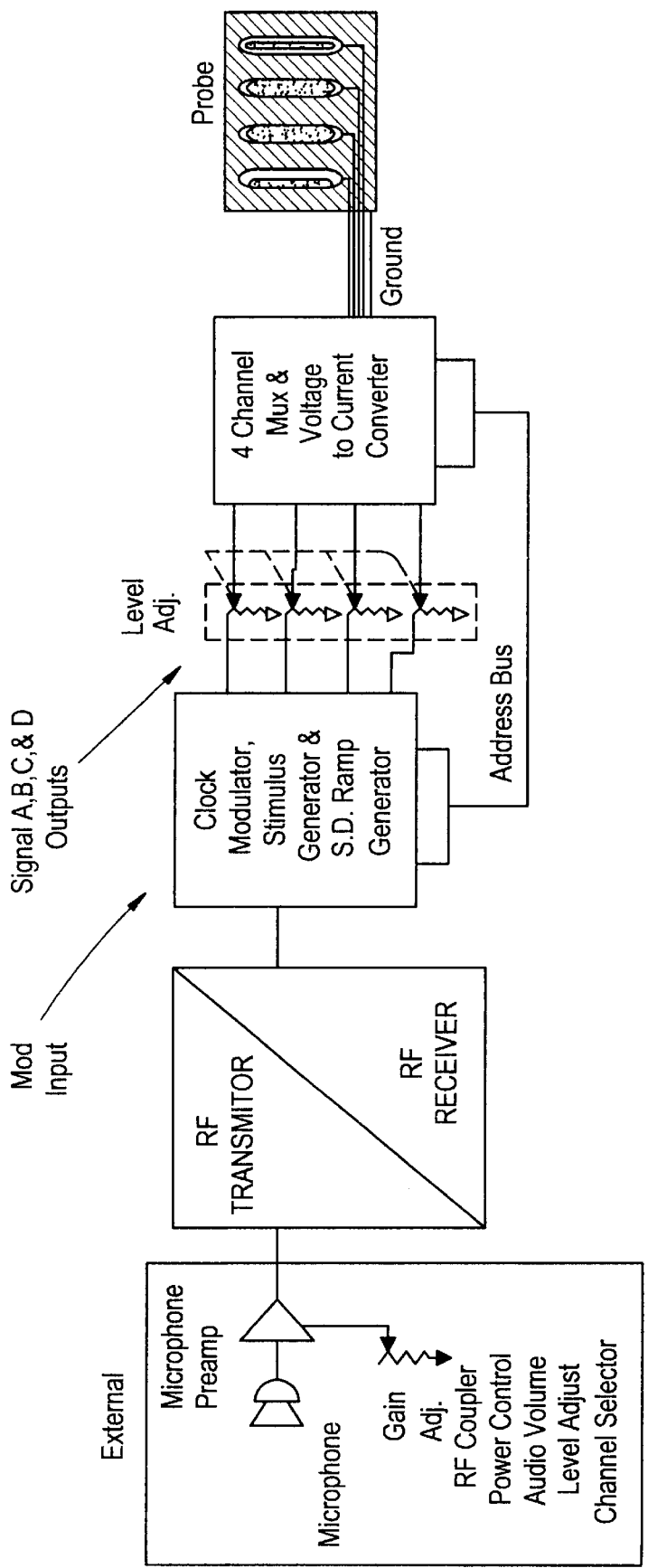
FIG. 8 is a block diagram of a 4-channel system.

FIG. 8 is a block diagram of a 4-Channel System. At the left is the microphone driving an audio amplifier and limiter/automatic gain control. The output of the audio amplifier drives the external transmitter. The internal receiver drives the Clock-Modulator, Stimulus Generator & Strength Duration ramp generator. The output of this module is fed through an attenuator to a 4-channel multiplexer. The output of the multiplexer then drives the probe.

Figure 9A:
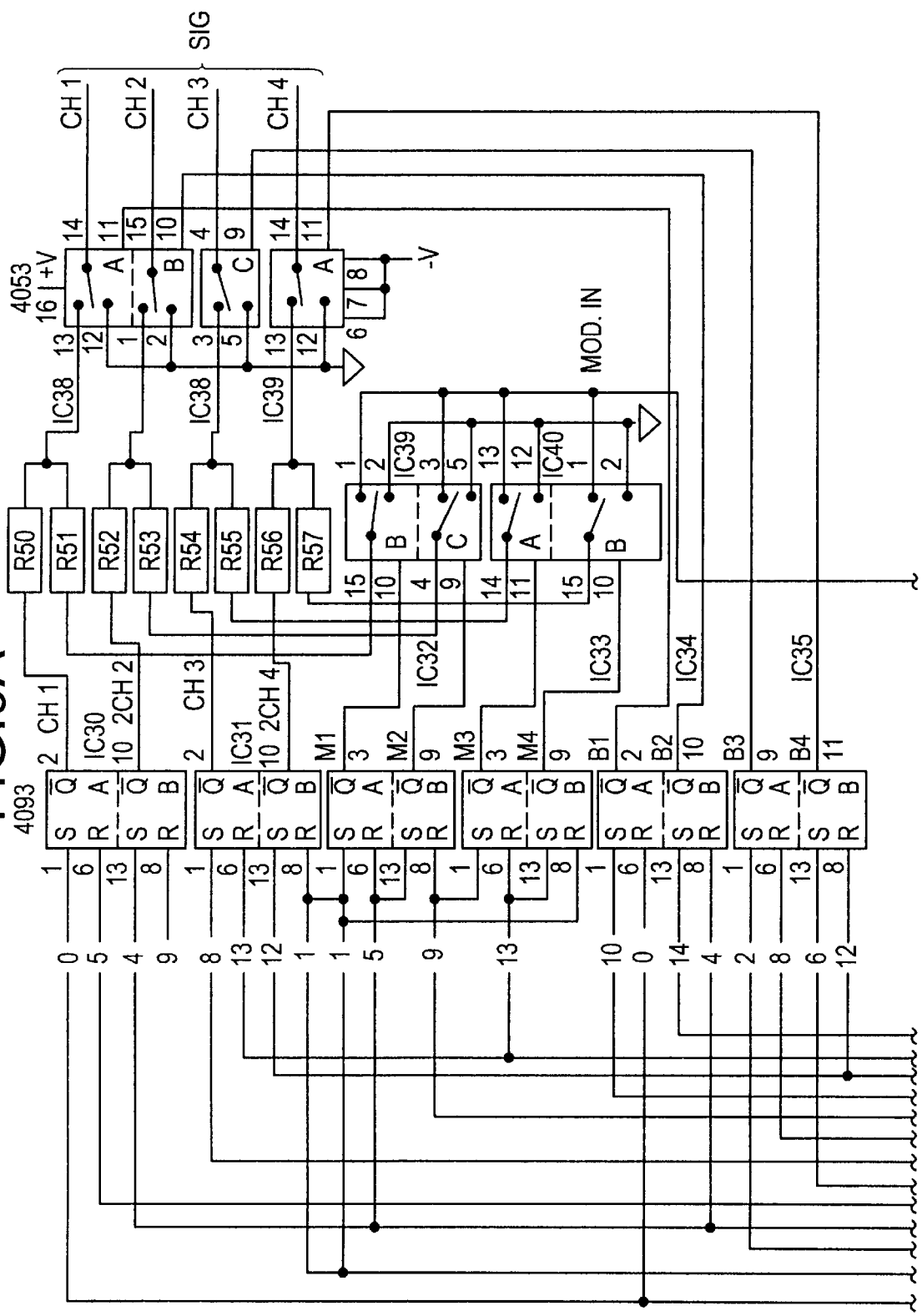
FIG. 9 is the schematic of the 4-channel clock, sequencer & modulator.
Figure 9B:
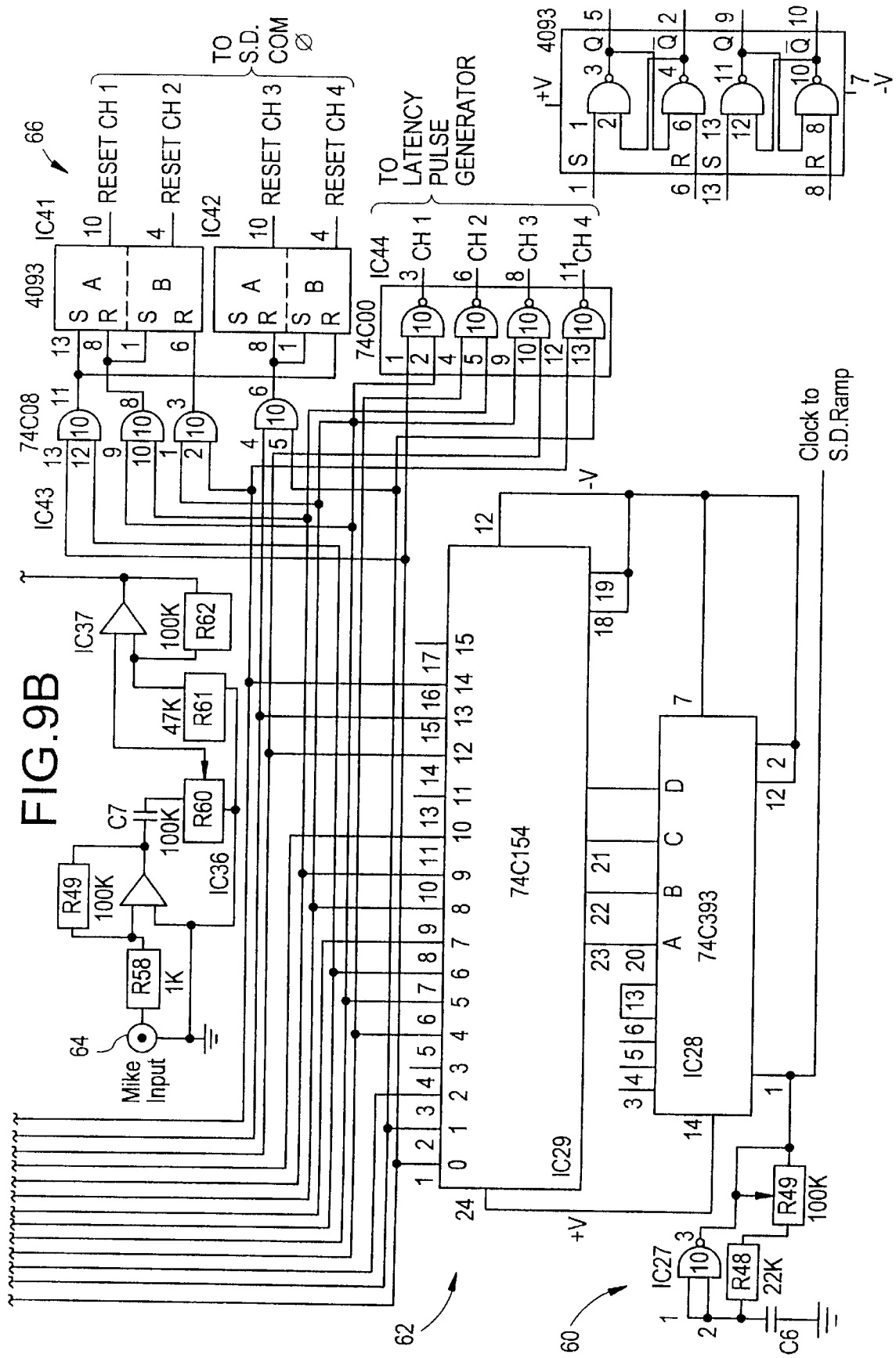

FIG. 9 is the circuit of the audio preamplifier, clock, and sequencer. To the bottom left of the figure is the Clock Oscillator 60. IC27 is one section of a 4093 used as a Schmitt trigger. R48 and R49 provide feedback to the input. C6 along with the sum of R48 and R49 determine the clock frequency. R49 provides a means of adjusting the clock frequency. The output of the clock drives the input of a 4-bit 74C393counter IC28 and also to the SD Ramp generator 62. The output of IC28 drives a 4-Line to 16-Line Decoder, IC29. At the right bottom of the figure is the wiring of 4093 Quad 2-Input Nand Schmitt Triggers wired to build Set-Reset Latches. At the top left of the figure are 6 4093's, IC30 through IC35 wired as shown to provide Set-Reset Latches. The first Latch IC30A is set on position 0 of the IC29 output. The second Latch IC30B is set on position 4, the third Latch IC3IA at position 8 and the 4$^{th}$ Latch IC31B on position 12. In a similar manner the first Latch is reset on position 5, the second Latch is reset on position 9, the third latch is reset on position 13 and the fourth Latch IC31B is reset on position 1. The output of these four latches is fed through resistors R50, R52, R54, and R56 to be summed with the audio modulation.

In the lower center of the FIG. 9 is the microphone input 64 driving a closed loop amplifier IC36 with a gain of about 80. The ratio of R58, the impedance of the microphone and R59 determine the gain. C7 AC couples to the next stage through a volume control R60. The value of C7 may be selected to provide preemphasis. IC37 adds an additional gain of 3 determined by the values of R61 and R62. The output of amplifier IC37 is the audio signal. It is fed into 4 single pole double throw CMOS switches IC39B, IC39C, IC40A and IC40B. Latches IC32A, IC32B, IC33A and IC33B control these switches. The arm of the switches is connected through resistors R51, R53, RSS, and R57 to sum with the channel stimulus outputs. Latches IC32A, IC32B, IC33A and IC33B control the timing of the switches. IC32A sets on IC29 position 1 and resets on position 5, IC32B sets on position 5 and resets on position 9. IC33A sets on position 9 and resets on position 13. IC33B Sets on Position 13 and resets on position 1. The summed outputs for channels 1 through 4 are fed into CMOS switches IC38A, IC138B, IC138C and IC139A. The output of these switches selects either the summed outputs of channels 1 through 4 or a ground reference level.

At the lower left of FIG. 9 are 4 outputs 66 going to the SD compensation circuit. These come from IC41 and IC42. IC43 a 74C08, an AND gate, drives their set and reset times as follows. RESET CH1 sets on position 0 and 6 (low output sets the latch) and resets on positions 5 and 9. In a similar manor RESET CH2 sets on positions 5 and 9 and resets on positions 8 and 14. RESET CH3 sets on positions 8 and 14 and resets on positions 1 and 13. RESET CH4 sets on positions 1 and 13 and resets on positions 0 and 6.

Figure 10A:
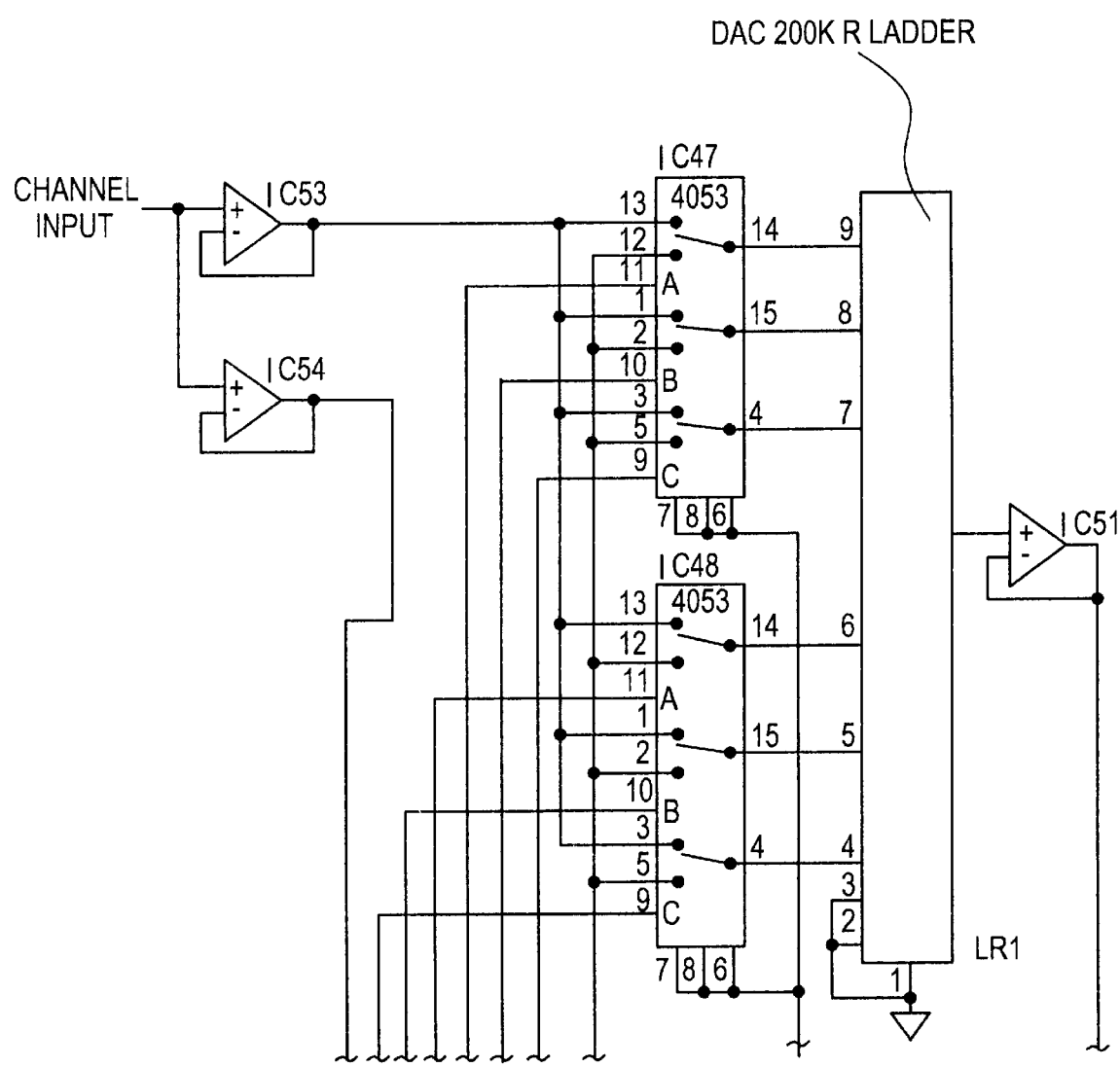
FIG. 10 is the schematic of one of four strength-duration curve compensation circuits.
Figure 10B:
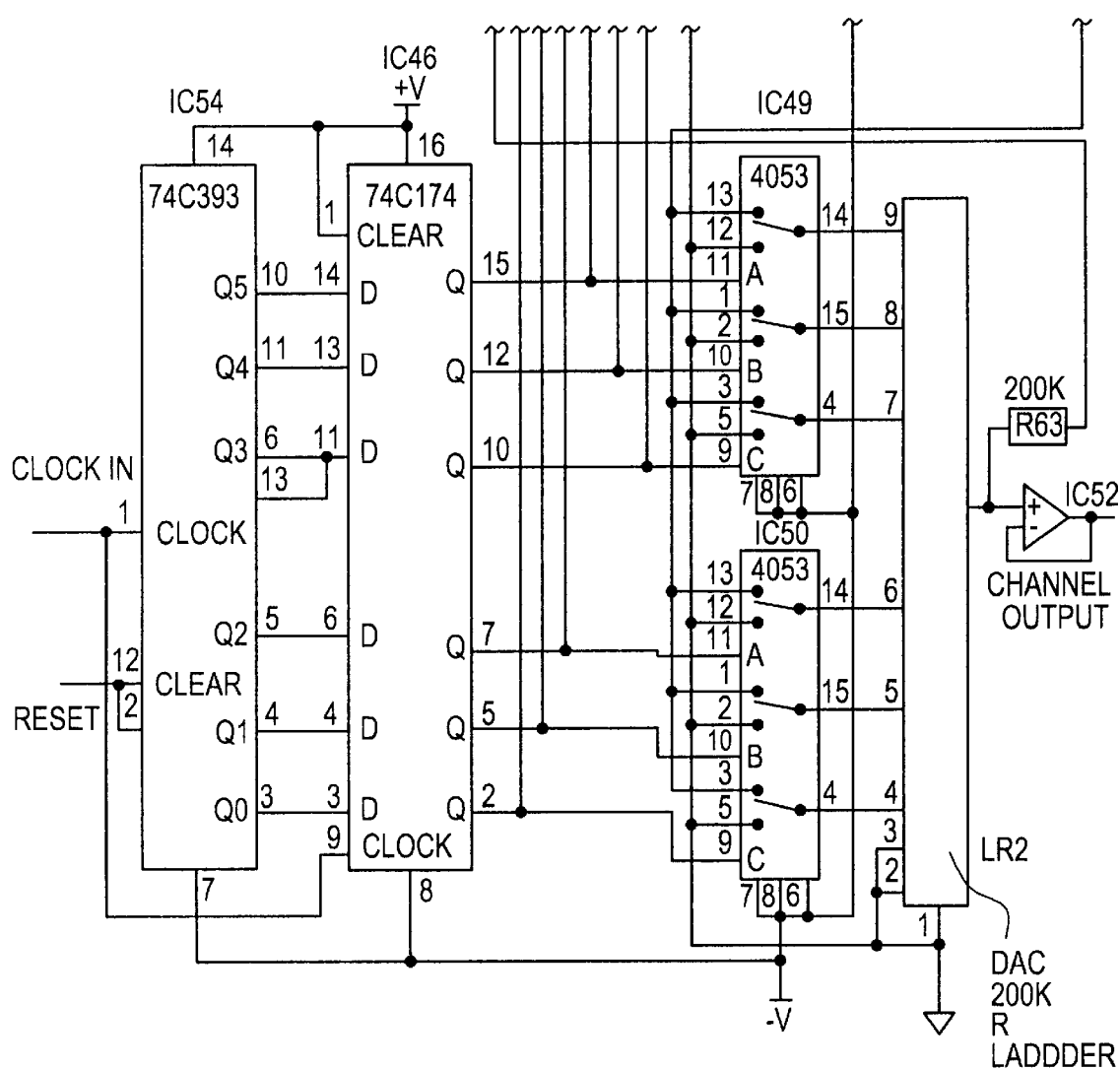

FIG. 10 is the schematic of one channel of the four channels of the Strength-duration compensation circuit. At the bottom left the inputs from the clock and reset signals from FIG. 9 enter. The clock signal enters the clock input of a 74C393, IC45 and the clock input of the 74C174, IC46. IC45 is held at zero by the reset/clear signal. When the reset signal stops, the counter starts counting. IC46 prevents counting timing errors by capturing the counter's value after any ripples have settled. The output of the IC46 register drives two digital to analog converters comprised of 4053 CMOS switches IC47, IC48, IC49, and IC50. These switches drive two binary ladder networks LR1 and LR2. At the top left of FIG. 10 the input signal from Channel 1 of FIG. 9 is fed into a buffer amplifier IC53 which drives first ladder Switches IC47 and IC48. The output of LR1 is fed into a buffer amplifier IC51, which drives the reference of the second DAC switches IC49, and IC50. In this manner a square law curve is generated to mirror the strength duration curve. This curve which is generated by the Channel 1 signal also has the audio modulation generated in FIG. 9. A second buffer amplifier IC54 feeds the Channel 1 signal through a 200K resistor R63 to the output of the second DAC. The outputs are summed and fed into a buffer amplifier IC52. This circuit for compensation for the SD curve is repeated for each of the four channels as shown in FIG. 11.

Figure 11A:
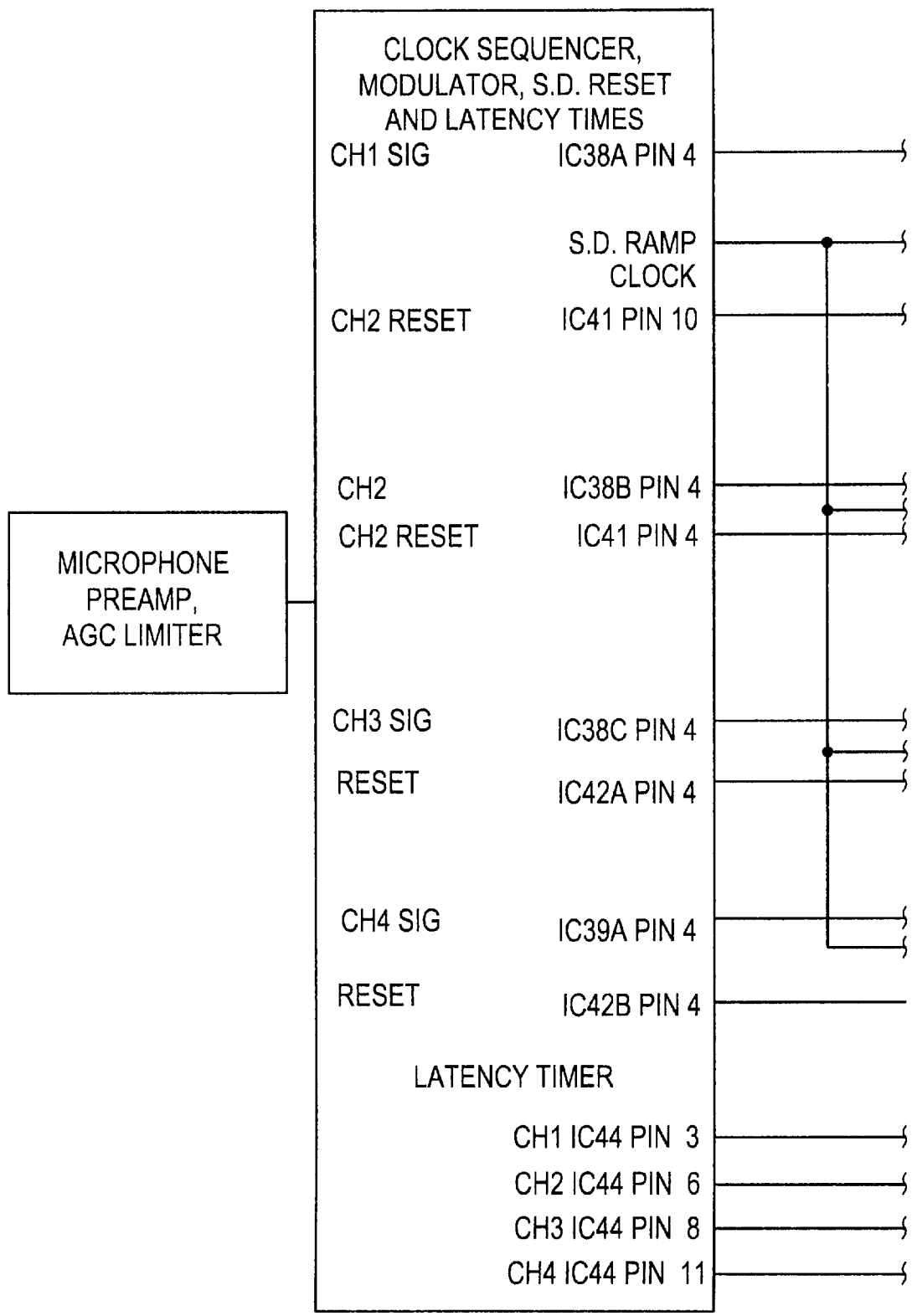
FIG. 11 is a block diagram of the interconnections between FIG. 8 and FIG. 9.
Figure 11B:
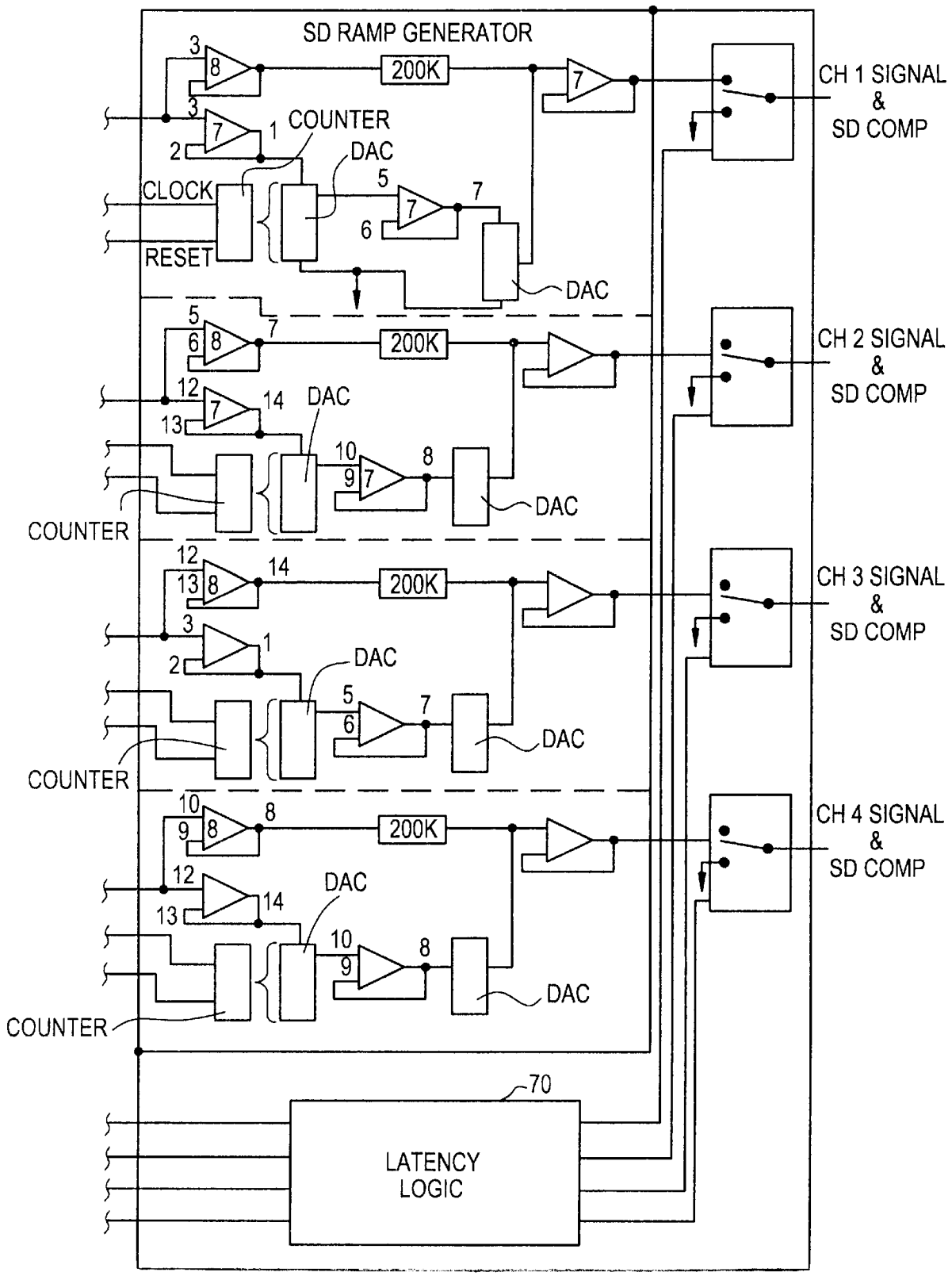
Figure 12:
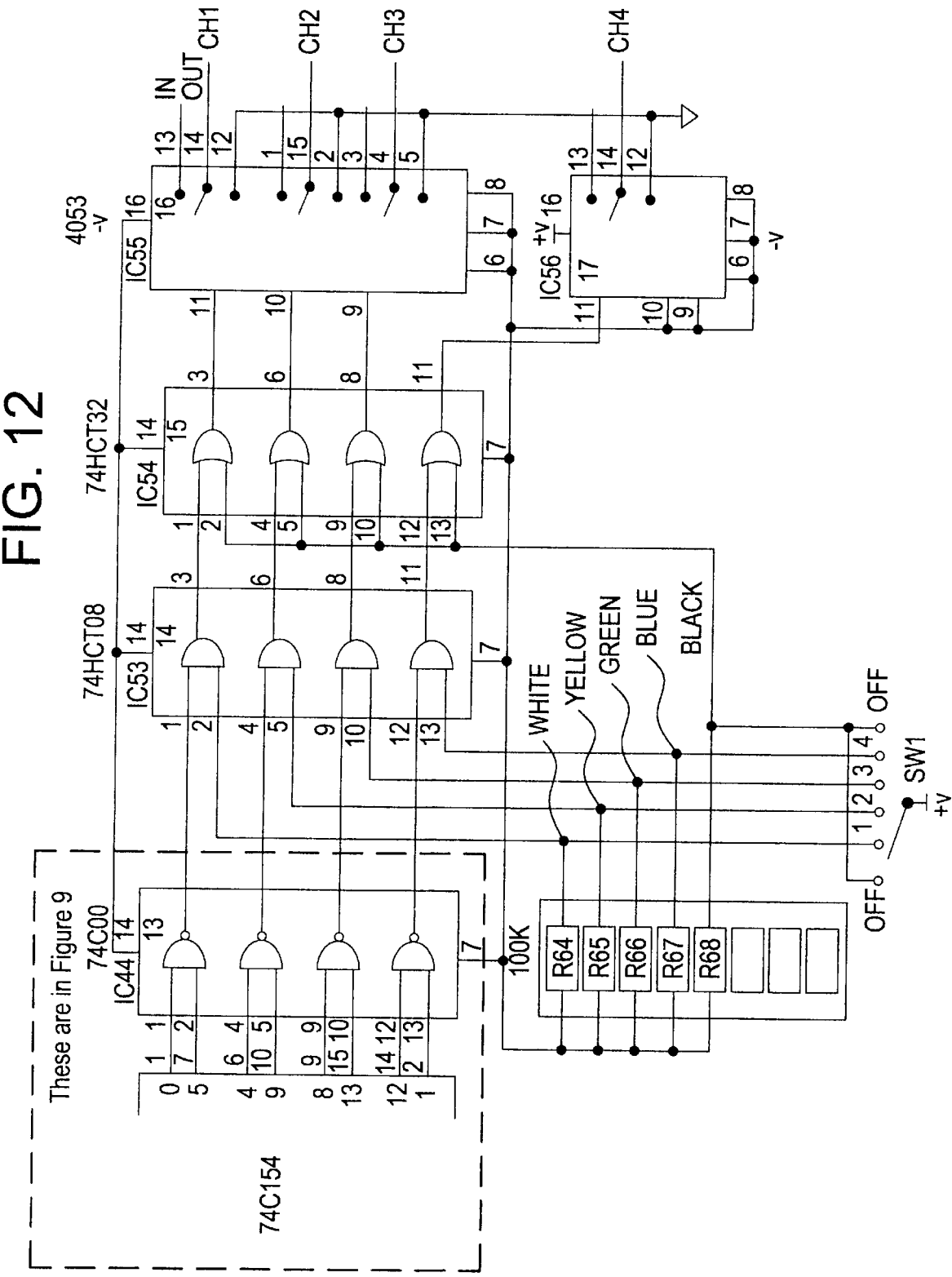
FIG. 12 is the schematic of the Latency period gate.

At the bottom center of FIG. 11 is a block called LATENCY LOGIC 70. When this is activated the pulse to each channel is shortened to the latency time, the time before the first nerve fiber is activated in a channel. It allows only one channel to be activated at a time. This is to allow for the adjustment of each channel stimulus amplitude to have its proper latency time and is also used to establish the strength duration characteristics for each nerve group during testing. FIG. 12 is the schematic of the LATENCY PERIOD GATE logic. The signals from FIG. 9 lower right drive IC53 a 74C08 AND gates. 100K resistors R64, R65, R66 and R67 ground one input of each AND gate. When SW1 is in the 1 position the input to IC53 which was held low by R64 goes high allowing the signal from IC44 to pass through to the output of IC53. In this manner each channel may be selected by SW1. When SW1 is in the OFF position a high signal is given to IC54 which causes the outputs of IC54 a 74C32 to turn on. The output of IC54 drives the analog switches IC55, and IC56 to select ground and the respective signal channel output or allows all channels to feed through.

Figure 13:
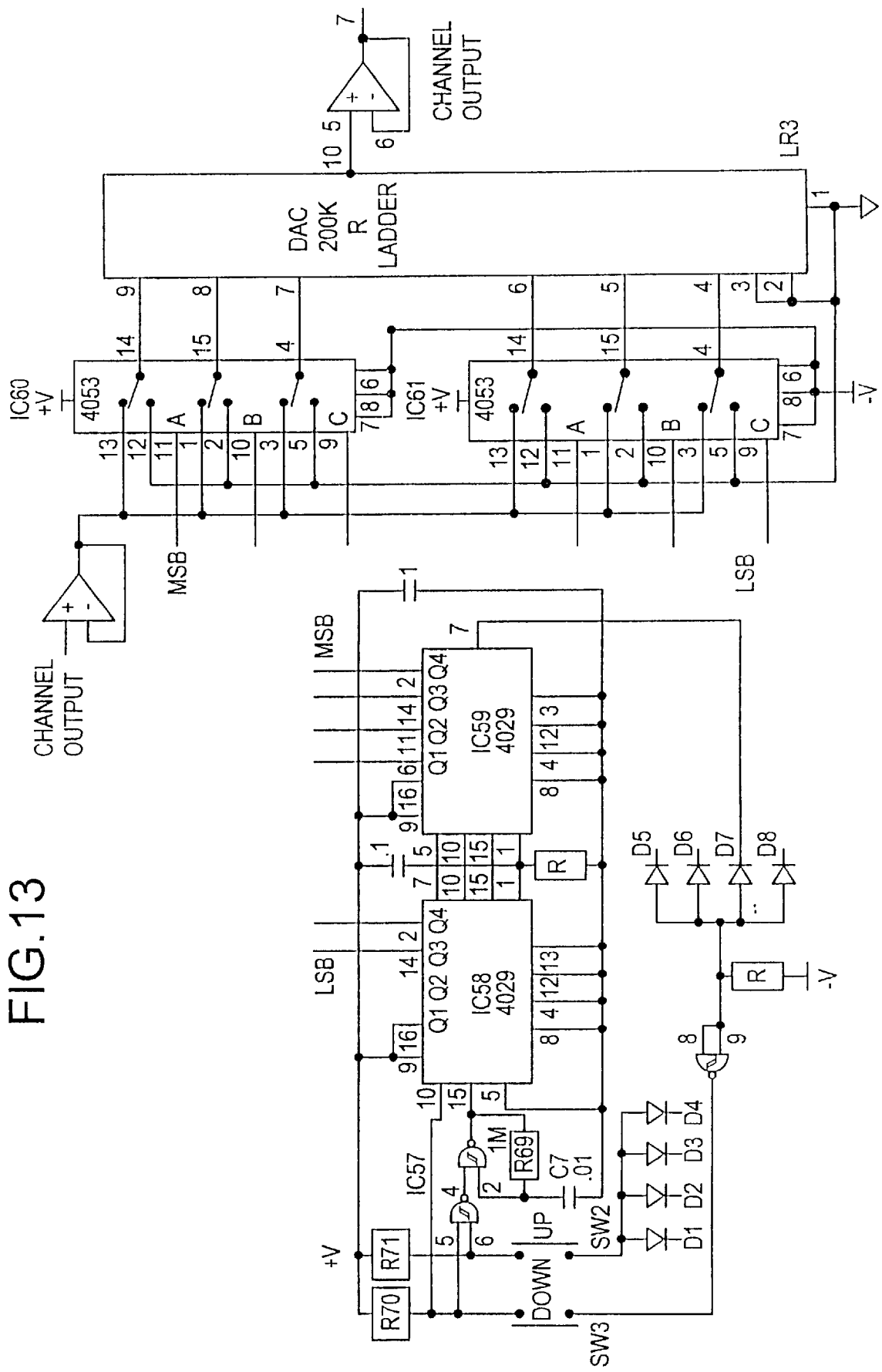
FIG. 13 is the schematic of the 4-channel output attenuator and one of four digital to analog converters used to perform the channel gain adjustment.

FIG. 13 is the circuit that adjusts the amplitude of each channel. IC57 is a Quad Schmitt two input gate that in combination with R69 and C7 generates a clock. The clock is enabled when either the UP switch SW2 or the DOWN switch SW3 is activated. When the down switch is activated, a low signal drives the up down counters IC58 and IC59 down inputs. In this manner, the counter will count up or down when commanded. Only 6 bits are used of the possible 8 from the up/down counter. The diodes D1 through D8 are used to prevent the counter from rolling over. When the count reached full scale it will not carry over to 0, and also when counting down to 0 it will not roll back to full scale. The output of the counters IC58 and IC59 drive four DACs configured as for the SD compensation circuit. This circuit in effect replaces a four-ganged potentiometer. The inputs to the four DACs are the output four signal channels of the latency period gate FIG. 12.

Figure 14:
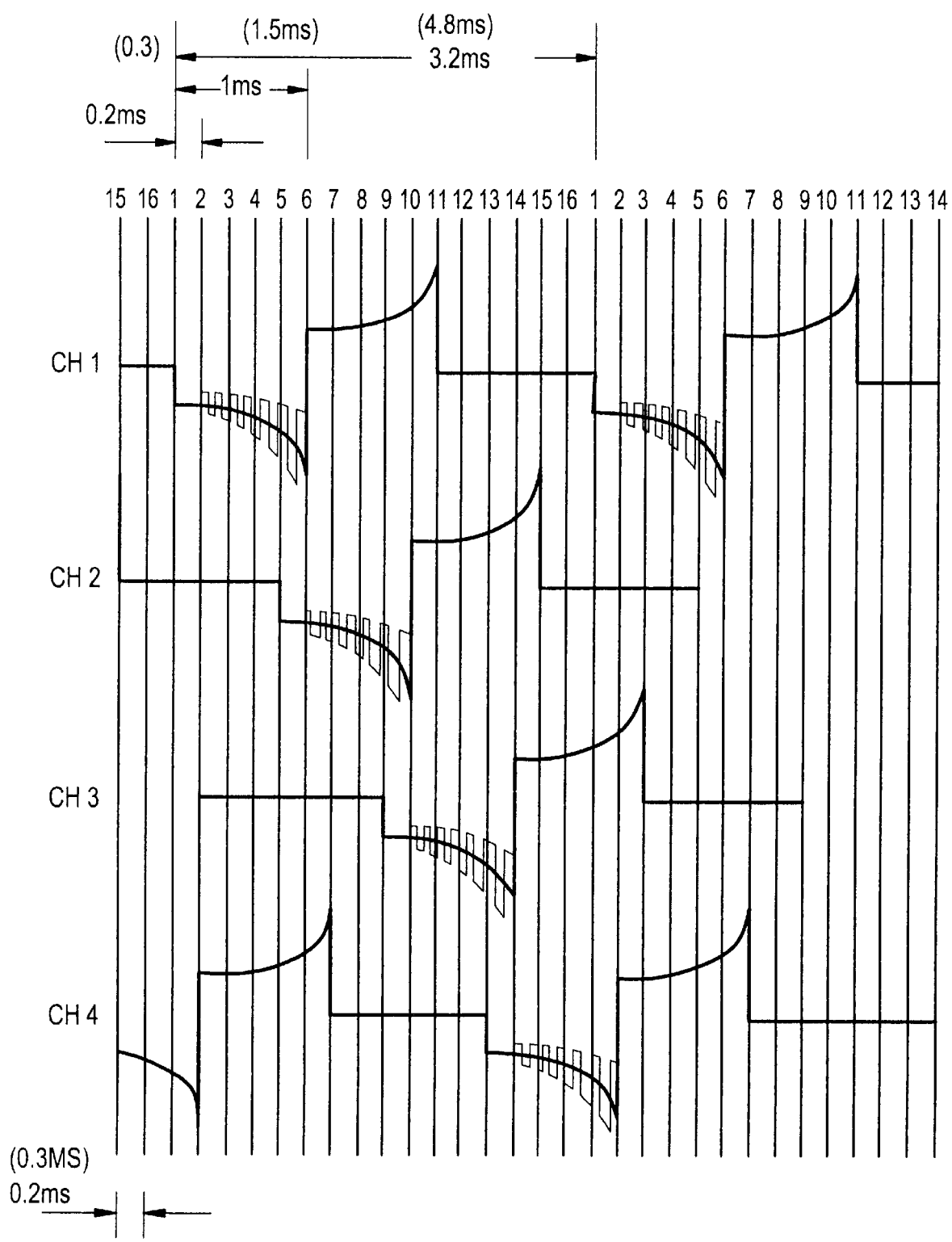
FIG. 14 is a chart of the timing and waveforms of the 4-channel system including the modulation of the latter portion of the stimulus waveforms.

FIG. 14 shows the waveforms for each of the 4 channels along with their modulation component. This figure shows an overlap of 0.2 or 0.3 milliseconds between channels and the superimposing of the modulation and compensation of the strength-duration characteristics of the nerve fibers on all but the first 0.2 or 0.3 milliseconds of each channel. Each channel stimulus pulse is bi-phasic to avoid introducing a DC component in the system. The modulation is only on the nerve-firing portion of the pulse. Since the modulation has an average value of zero over time, it is not necessary to modulate the portion of the stimulation pulse following the modulation. The portion of the stimulation pulse that follows the modulation is an inversion and results in an average DC value of 0. Not shown in this figure but shown in FIG. 5 as typical is the background state of nerve activity when no sound is present. This background state when modulated results in the perception of sound.

FIG. 15A shows a four-channel probe 80. The conducting area of the electrodes is vertical producing a gradient field between the electrodes and providing a maximum surface area for each electrode. In this way the contact surface area is not determined by the closeness of the electrodes and an accurate gradient field is produced.

The distance between ground electrodes can be as small as 20 microns and over 200 microns. The hair cells are spaced typically 10 microns. Twenty-micron spacing allows only 1 row of hair cells between the active electrode and its associated ground. However if the probe is tilted so that the hair cells are staggered between the active and ground electrodes, streaming will occur. Even though the hair cells are non-functional in the profoundly deaf, the location of the hair cells is an indication of the location of the ends of the nerve fibers transmitting sound sensations to the brain. Behind the ground and active electrodes is a layer of insulation. This is to avoid producing an electric field on the backside. Behind the insulator is an additional ground plate to increase to a maximum the ground area. A maximum ground area is desired as it lowers the contact impedance of the ground to the conducting fluid and provides a gradient field that minimizes channel crosstalk. Also, not shown in the FIG., insulating material may be placed at the side ends of each channel to prevent current flow out the side ends.

Figure 15B:
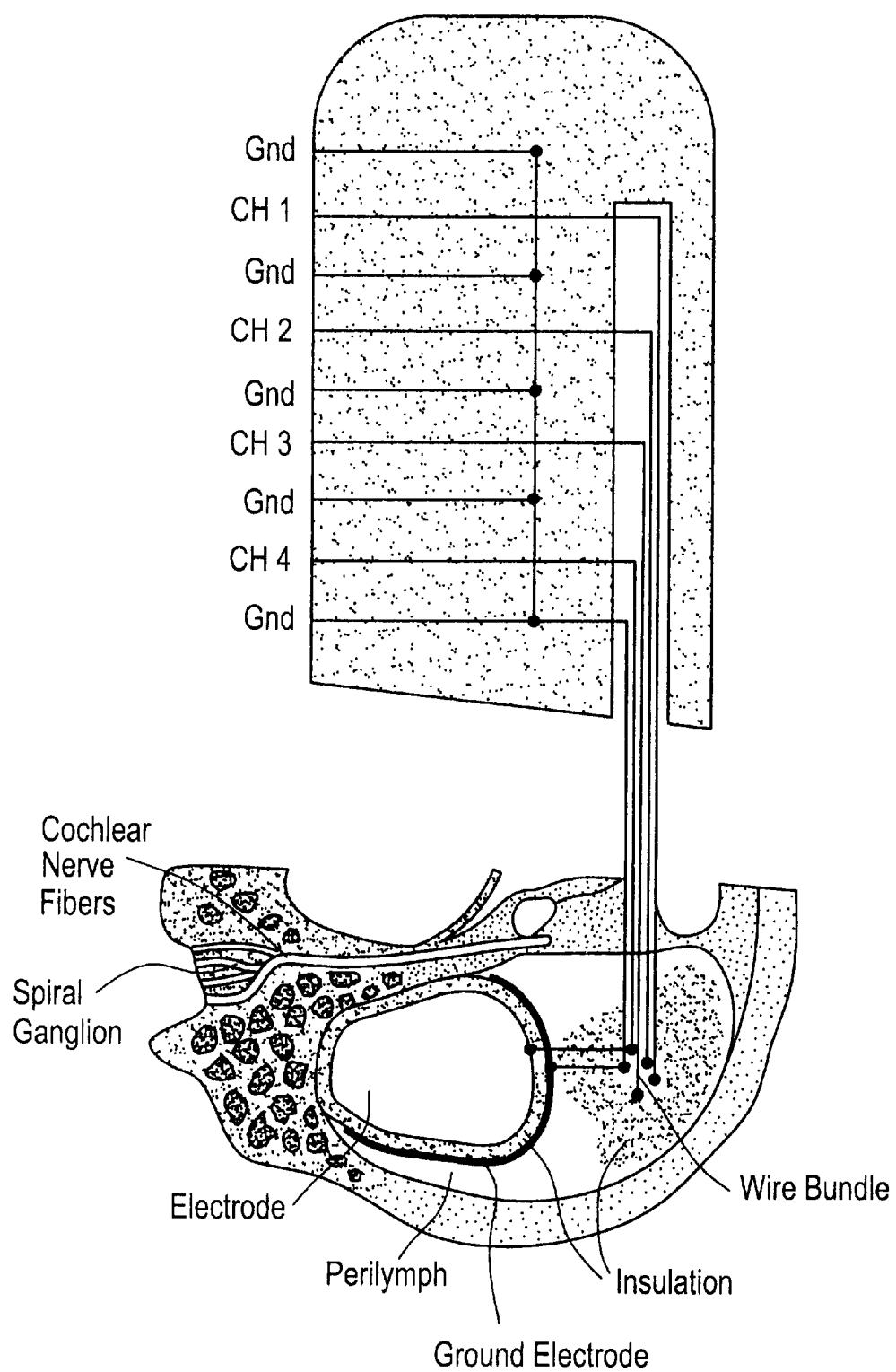
FIG. 15B is a drawing of the 4-channel probe showing its conformity to the shape of the Scala tympani and its location relative to the Spiral Ganglion.

FIG. 15B shows a four-channel probe located near the Spiral Ganglion. As in FIG. 15A, the electrodes are mounted perpendicularly to the gradient field. The diameter of the probe at its largest point is about 2 mm, and the diameter of each electrode at its largest point is about 1 mm. The distance between ground electrodes is between 0.5 mm and 2 mm. The probe electrodes are mounted in a flexible insulation structure allowing the probe to form to the shape of the Scala Tympani or the Scale Vestibuli. The length of the probe area housing the electrodes is between 2 mm and 8 mm. In systems with more than 4 channels, the spacing between ground electrodes would be less.

THE DIGITAL SYSTEM

The limit of this system leads to a system where only 1 nerve fiber is stimulated per channel and the system becomes purely digital. Again to achieve the 24 kHz carrier frequency in the digital system, where the repetition rate of firing an individual nerve fiber is 200 pulses per second, 120 channels are required. (120×200=24,000). In this digital system, rather than track the Strength-duration curve for each channel, as done in. the analog systems, a high amplitude stimulus pulse is utilized to place the firing of the nerve fiber on a steep portion of its Strength Duration curve. This minimizes the activation time differences between channels. The electric field is restricted to only 1 or a small constant number of nerve fibers, which appear to fire simultaneously, producing the 24 kHz neuro-carrier frequency. In this digital system, modulation is accomplished by frequency modulating the carrier frequency. No amplitude modulation of the pulse stimulus is required. It becomes apparent from this that in a system that is in the transition region between analog and digital both amplitude and frequency modulation may be used to advantage.

FIG. 16 is a block diagram of the digital system. At the left of the figure is the external unit 102. It consists of a microphone, audio amplifier, limiter/automatic gain control, oscillator, frequency modulator, loop antenna and a power source. In the center of the figure is the internal unit 104, a loop receiving antenna, diodes to provide both positive and negative voltage, voltage regulators and a 128 position counter/decoder and individual latches for each channel. To the right of the figure is the probe 106 that is placed near to the nerve fibers that conduct sound to the brain.

Figure 17:
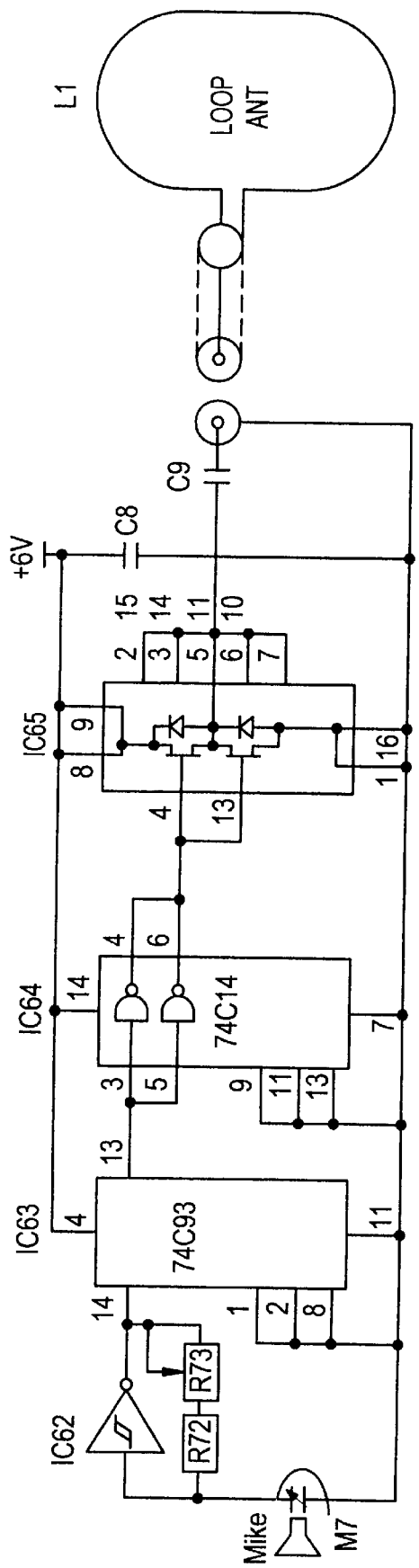
FIG. 17 is a schematic of the external power source, microphone, frequency modulator and RF coupler of the digital system.

FIG. 17 is one version of the external unit. To the left of the figure is a capacitor microphone M1 connected to the input of the Schmitt IC62 with feedback through resistors R72 and R73 forming a frequency-modulated oscillator. R73 is variable to adjust the center frequency. The output of the oscillator is divided by 2 in IC63, a 74C93 counter. The output of IC63 is buffered by IC64 to prevent capacitive loading on the counter output. The output of the buffer IC64 drives IC65 a MOSPOWER HALF-BRIDGE DRIVER Si9950. The output of IC65 is a low impedance switch that switches from one power rail to the other. The output is fed through C9 to the Loop Antenna L1. Capacitor C9 resonates with the inductance of the Loop Antenna forming a tuned circuit. Capacitor C8 is across the power connections of IC65. The layout is such that there is a minimum of area within the current path as the resonate currents through the loop can be high and any areas outside the Loop Antenna will reduce efficiency.

Figure 18A:
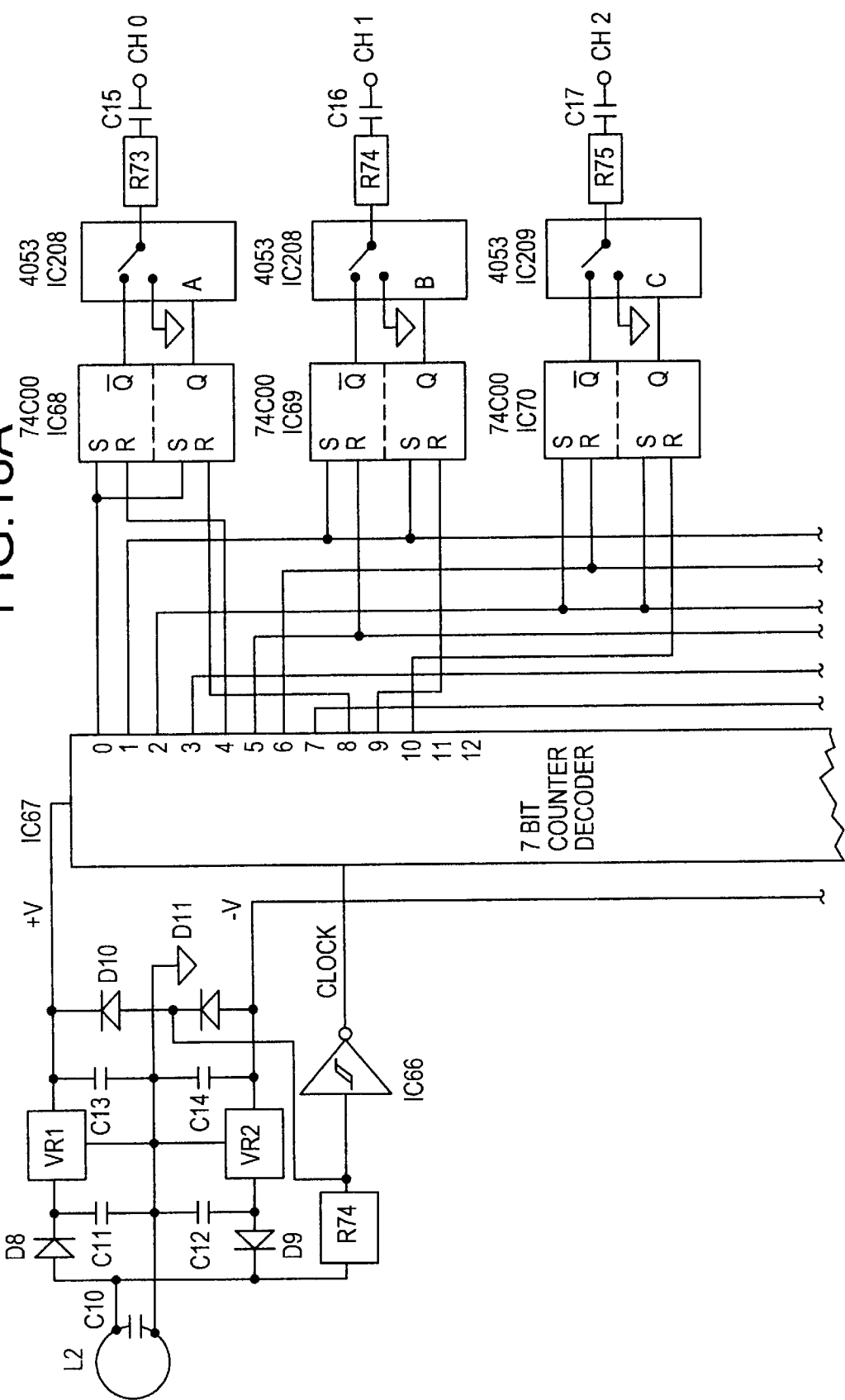
FIG. 18 is a schematic of the internal unit of the digital system.
Figure 18B:
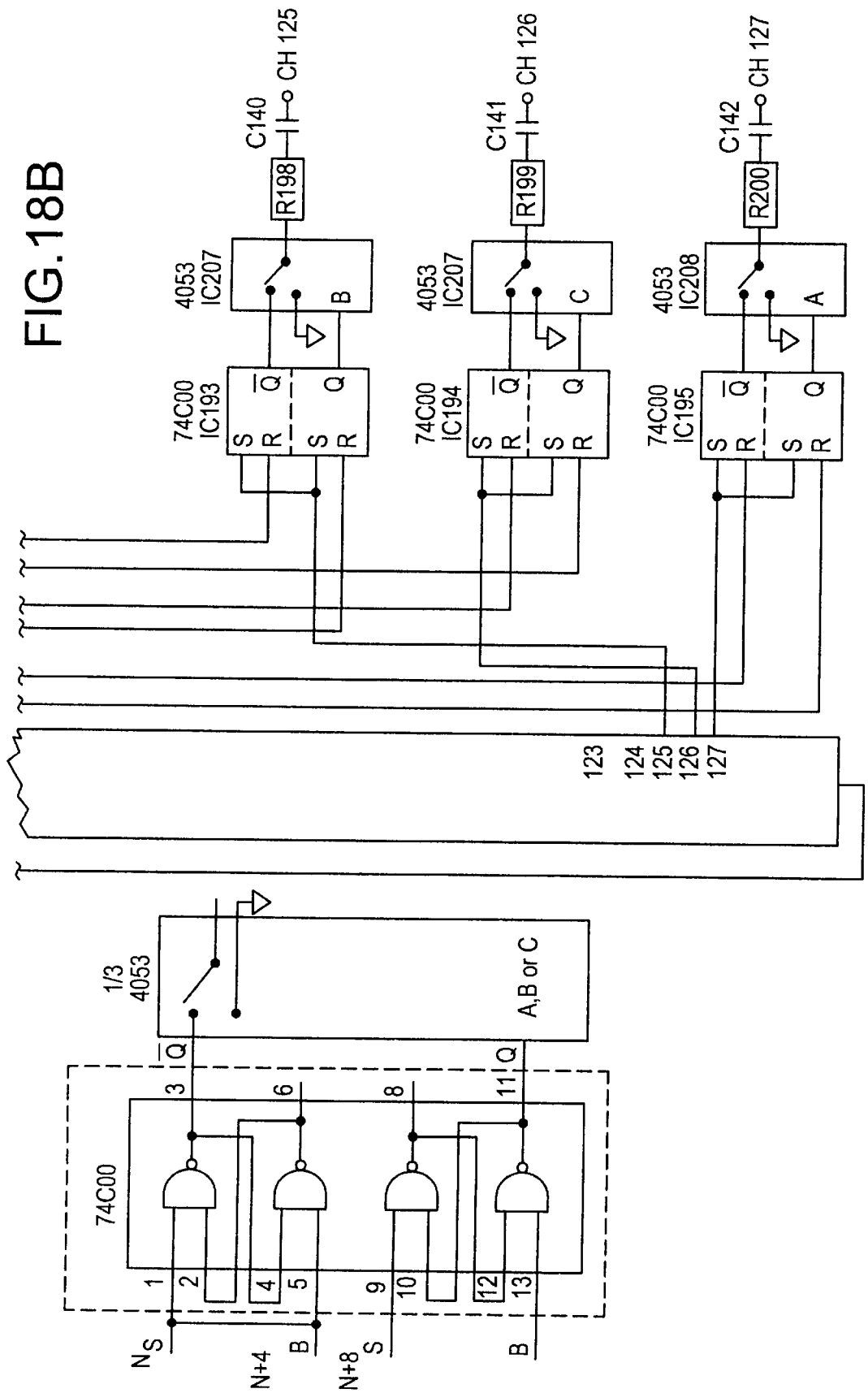

FIG. 18 is the internal digital system unit. At the top left of the figure are the loop antenna L2 and its tuning capacitor C10. The output of the loop antenna goes through diodes D8 and D9 to produce + and − voltages. Capacitors C11 and C12 filter the DC voltages. Voltage regulators VR1 and VR2 regulate the voltages. C13 and C14 provide stability to the voltage regulators outputs. R74 is connected to the Loop antenna output to provide a clock to the implanted system. Diodes D10 and D11 limit the voltage swing at the input of IC66 a Schmitt trigger. IC64 provides the clock signal to the 7 bit counter decoder IC67. The 128 positions of the counter IC67 (0 through 127) drive set-reset latches IC68 through IC95 formed by 74C00 CMOS gates.

As shown in the lower left of FIG. 18, these latches are set on a given number N, with the first latch reset at N+4 and the second latch reset at N+8. Subsequent latch pairs are shifted one count down as shown in the drawing. The outputs of the first latch pair goes into a 4053 IC196A. When the switch IC196A is OFF, the output of the switch is at ground or zero potential. When the switch is ON the output of the first latch is connected to the output. This will occur for one complete cycle of the first latch. In this way the average potential of a given channel will be 0. The output of these switches have their voltage changed into a current through resistors the same as R73 on channel 1 and also through capacitors such as C15 to further ensure no long term DC component.

Figure 19:
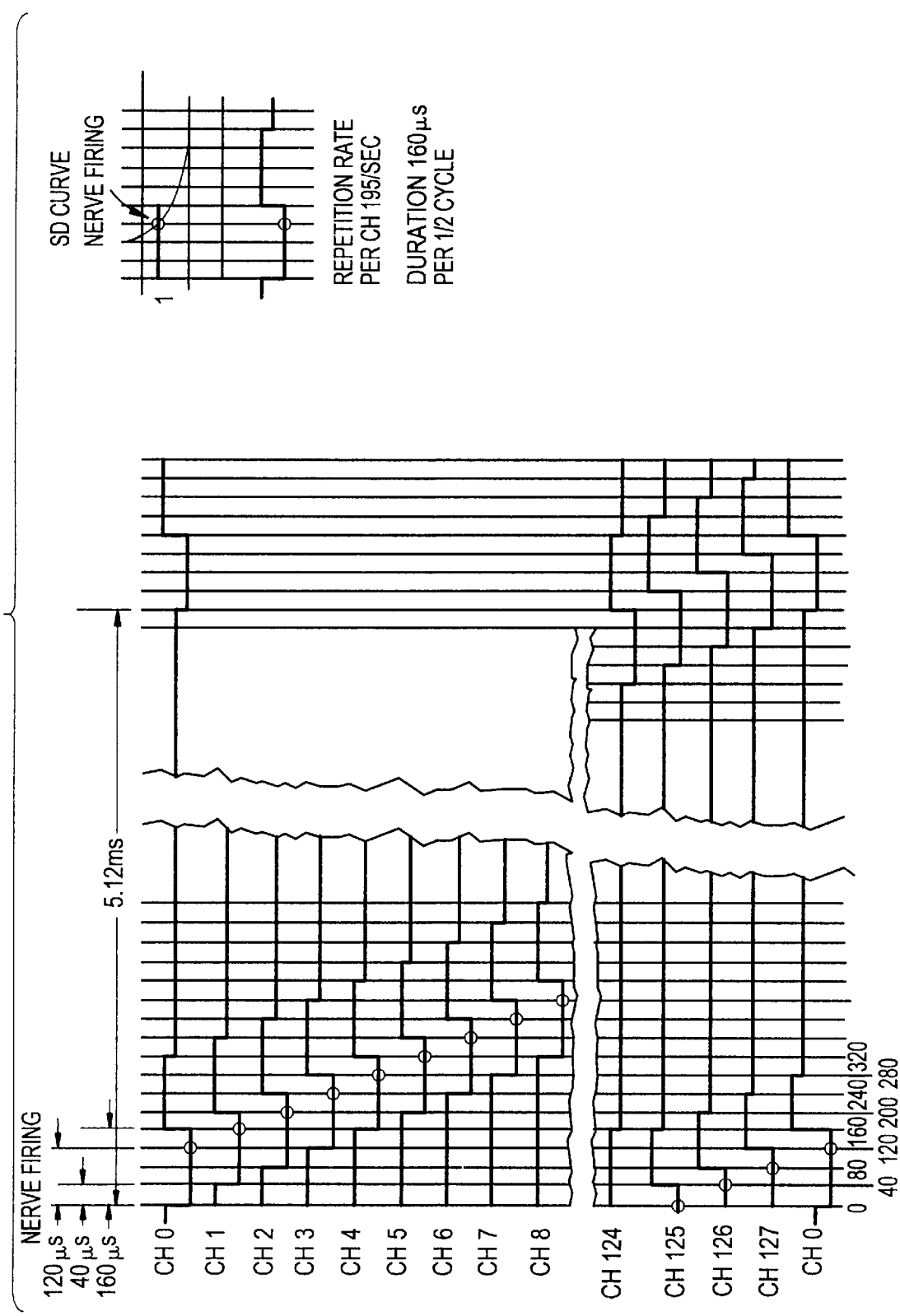
FIG. 19 is a chart of the waveforms of the channels of the digital system.
Figure 20:
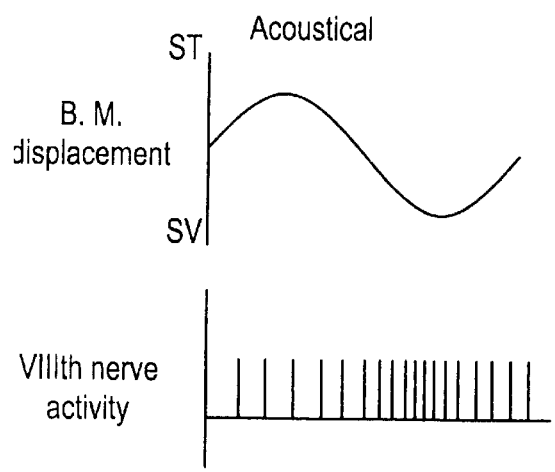
FIG. 20 is a chart showing the VIII nerve activity changes as the result of acoustical basil membrane displacement. (Honrubia V, Strelioff D, Stiko S; Ann Otol Rhinol Laryngol 85:697–701, 1976)

FIG. 19 shows the waveform of the individual channels of the digital system. The circles on the waveform indicated the time that the nerves fire. The delay between channels is 40 microseconds. The amplitude of each stimulus pulse is such that the excitation time of a nerve fiber will occur on a steep portion of the strength duration after 120 microseconds and the stimulus pulse will last beyond the excitation of its nerve fiber, in this drawing 160 microseconds. The repetition rate of each channel is 5.12 milliseconds or about 5 time constants, which allows the recovery of the nerve to about 1% of its initial condition before stimulus. In all systems both analog and digital a carrier of about 25 kHz is used only as an example. Higher frequencies would require a higher stimulus amplitude which would cause a higher streaming rate and would provide greater frequency response of the modulation. It is also recognized that as with any carrier system the audio modulation bandwidth must be restricted to less than ½ times the carrier frequency.

PROCEDURE

The procedure for implanting the device into a human ear is as follows:

The placement of the gradient probe is critical and requires precise placement for optimum performance. With an adult patient who has heard in the past the probe is placed while the patient is alert. Using a local anaesthetic the probe is moved into place by having it activated and the patient indicating when he hears intelligible sound. Then for exact placement each channel is stimulated alone to establish that each channel requires about the same stimulus intensity to produce the sensation of sound and to verify the strength-duration characteristics. A second time the patient is asked to confirm that his hearing is normal and then the probe is fixed permanently in place. During this procedure a jig that is mounted to the patients head is used to hold the probe so that motion of the head will not effect the location of the probe in relation to the nerve fibers.

With patients who have not heard in the past the probe is located as above except the last step is to confirm that a minimum of sound is heard when no external sound is present and sounds are comfortable when externally generated.

For children who are unable to provide direct assistance, other means of establishing the presence of sound sensations through measurement of nerve activity at a higher level or brain activity may be used. One method is through the measuring of nerve activity in the cochlea.

The method of the present invention directly stimulates nerve fibers of the audio transmission portion of the $8^{th}$ nerve with electrical signals representative of sensed audio sounds in sequence, thereby imparting the sensation of hearing to a deaf patient. The method comprises implanting a receiver with a loop antenna and with connections to an electrode probe, comprised of an array of electrodes formed to produce multiple gradient fields in the patient, on the audio portion of the $8^{th}$ nerve and generating an electrical signal representative of sensed audible sounds. An electrical signal is divided into time multiplexed channels whereby each multiplexed channel is connected to a corresponding gradient probe channel and contains the audible representation of the entire audio spectrum and means for limiting the audio spectrum. Each channel is processed to produce a bi-phasic stimulation signal that overlaps its adjacent (in time) channel bi-phasic stimulation signal but does not overlap its component that is representative of audible sounds.

The method further comprises aligning an external transmitter/receiving loop antenna with the implant receiver/transmitting loop antenna such that there is a distance at least equal to the thickness of the patient's skin separating the external antenna from the internal antenna thereby providing a means of transmitting both power and audible sound representations to the implant receiver, and locating the gradient probe in proximity to the nerve fibers that transmit sound sensations to the brain. Further, the method comprises compensating for motions of the patient's head during placement of the gradient probe; and fixing in a permanent manner the gradient probe.

While there have been shown embodiments of the invention, it will be understood that changes and modifications may be made to the methods and devices shown herein by those skilled in the art and it is, therefore, intended that the appended claims cover all such changes and modifications as fall within the true spirit and scope of the present invention. In the circuits described above standard well known components are shown. This is to provide specific examples of how detailed functions may be effected. It does not suggest that programmable gate arrays, microprocessors or other components are excluded. In fact devices such as Intel's 8XL51FX COMMERCIAL/EXPRESS LOW VOLTAGE CHMOS SINGLE-CHIP 8-BIT MICROCONTROLLER are an excellent choice to mechanize the functions of the invention. When operated with a clock frequency of 3.5 MHz it draws less than 6 mA.

Figure 22:
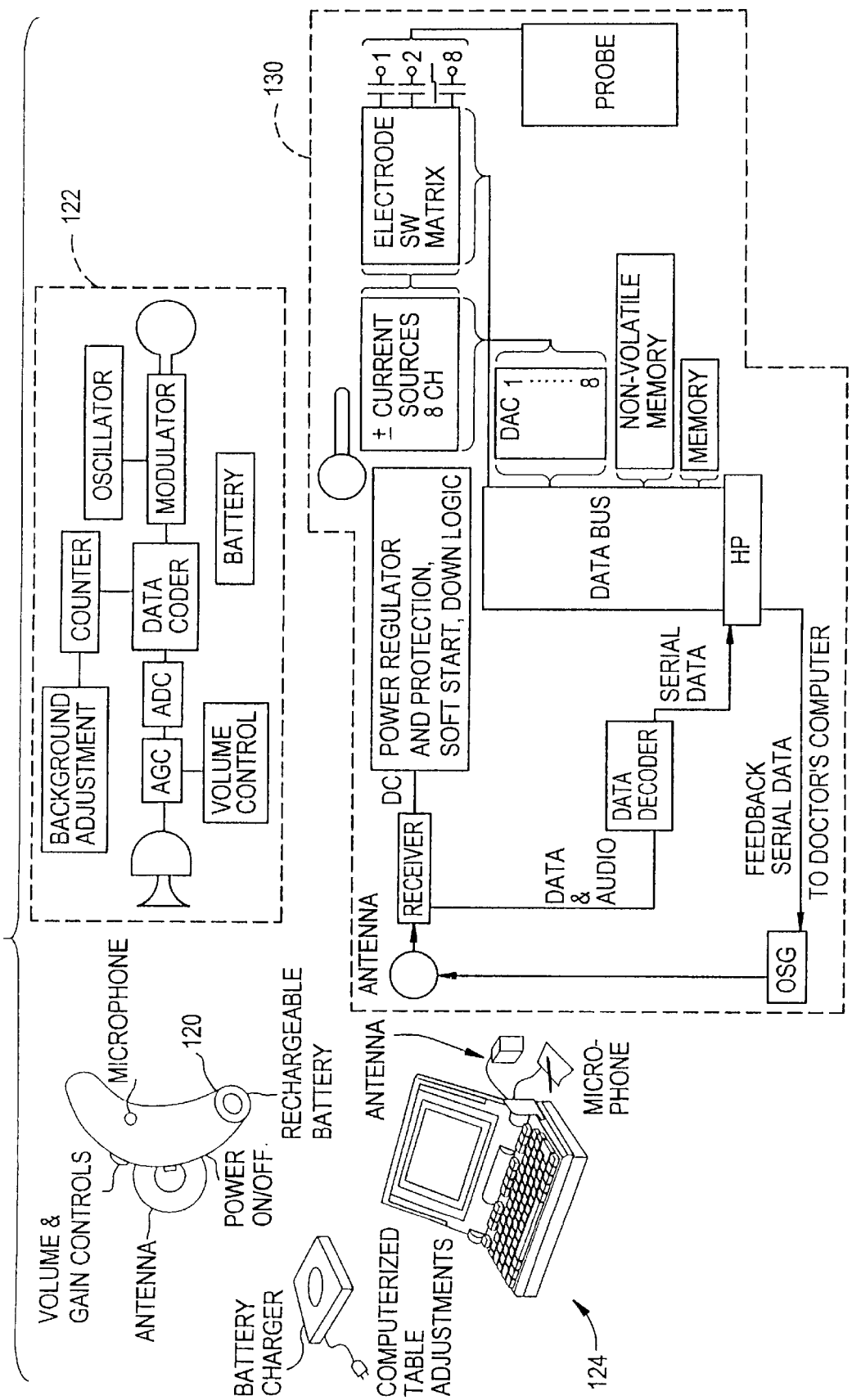
FIG. 22 shows a system block diagram. This includes an implant using a microprocessor, the external unit for the patient, a test computer and a brief showing of computer screens.

FIG. 22 is a system block diagram including the use of all of these devices. At the top left of the figure is a sketch of the external module 120 to be worn by the patient. It is designed to be worn behind the ear in a manner similar to some conventional hearing aids. It houses a high-energy rechargeable battery as a power source. The unit, when not in use, can mount in a charger showed beneath the unit. The external module has a volume control, a null background tone adjustment, a power switch and a microphone located in the unit behind a small hole. The antenna coil is connected to the unit through a small cable and mounts adjacent to the implant receiver coil. To the right of the external module package is a block diagram 122 of the circuits. The microphone drives the automatic gain control circuit. The volume control sets the input to an analog to digital converter. Above the AGC block are the up and down controls which drive an up/down counter. This is a fine trim of the stimulus level.

This value plus the output of the DAC is formatted to feed the modulator, which superimposes the data onto the oscillator output and is fed to the antenna.

Located beneath the external module and charger is a sketch of the physician's office computer module 124 consisting of a lap top computer with a microphone, a transmitter/receiver and software to perform the following functions:

1) Establish a bi-directional communication link between the external computer and the implant computer, 2) adjust the channel selection rate (or channel frequency), stimulus amplitude for each channel both independently and in a ganged manner.

3) Adjust the compensation for the strength-duration curve. This adjustment is in the form of a computer table. It establishes a time constant curve that can be trimmed at all points of the curve to null out the variations in the nerve activity carrier. This curve interacts with the stimulus amplitude adjustment as its values are in terms of percentage of stimulus amplitude. The time axis of the table is independent of the channel selection rate.

4) Adjustment of both audio (coarse) level and soft start speed. The soft start/stop function causes the background carrier to gradually turn on or off with a minimum of annoyance to the user.

5) Adjust the number of channels to be used. Four are a minimum and eight are a maximum. It also selects which channels of the probe will be used. First the physician scans each channel and establishes its functionality as to sensitivity, and strength-duration characteristics. In the case of the choice of 4 channels to be used, then the physician selects which channels of the probe will be used. All unused channels are grounded to the common return electrodes. In the case of a 6-channel system the best 6 probe channels are used. During this selection process the electrode matrix switch remains on the selected channel electrodes and all other channels are grounded. FIG. 22C shows the selection of 4 channels of an 8 channel probe.

Figure 22A:
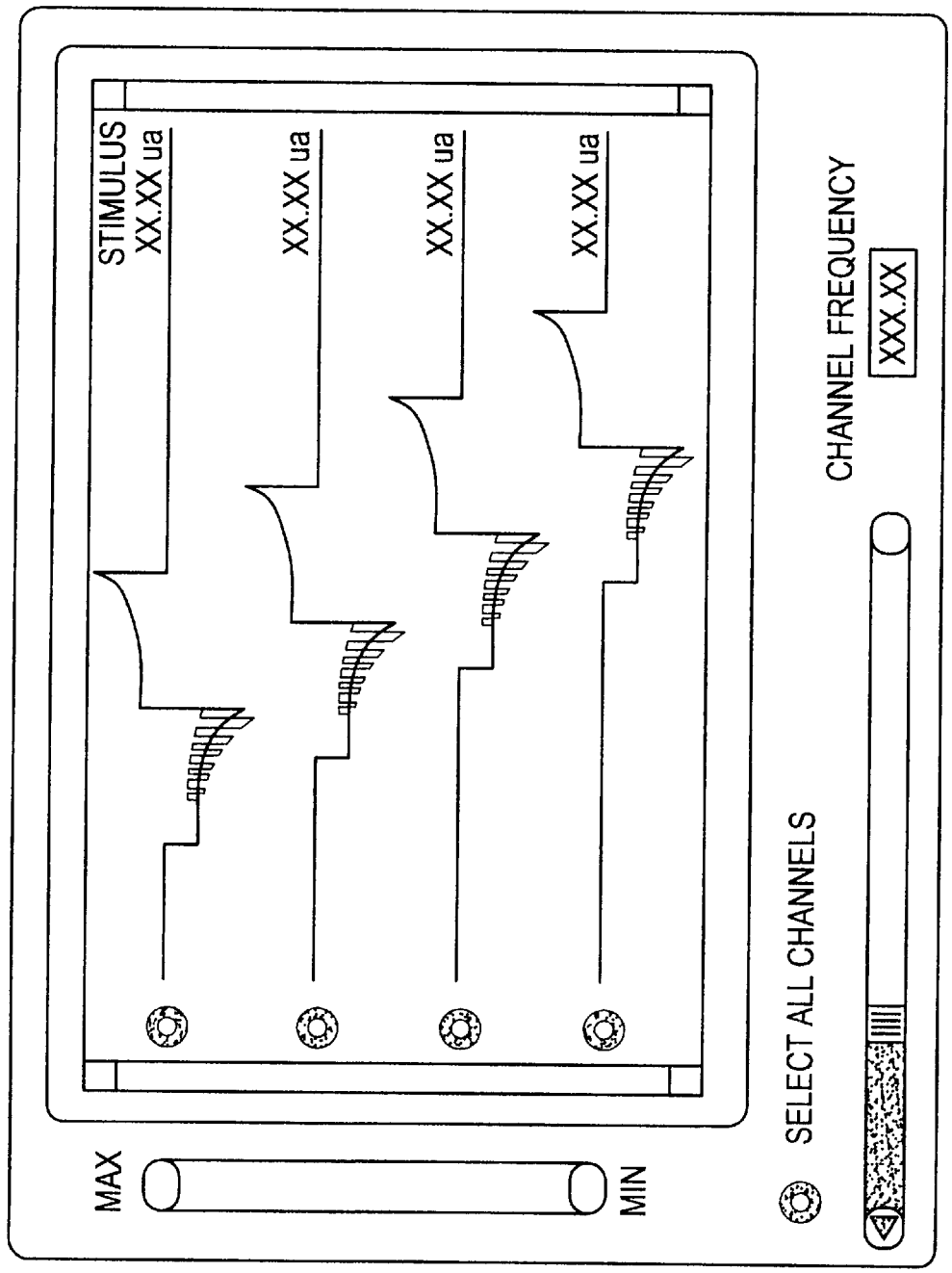
FIG. 22A depicts the ability to adjust the amplitude of each stimulus channel independently, both amplitude and gain, and to select the channel frequency.
Figure 22B:
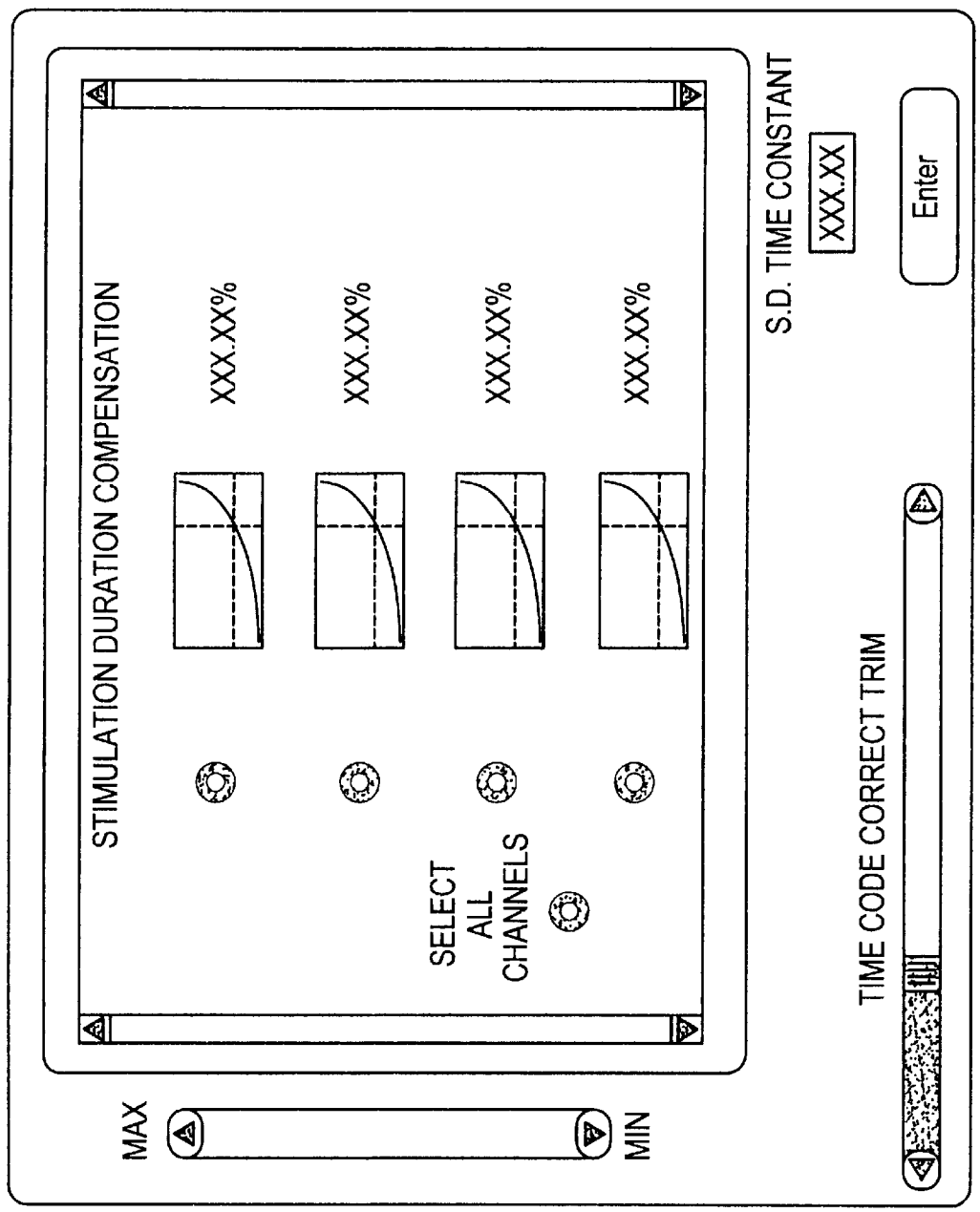
FIG. 22B depicts the ability for adjustment of the Strength Duration Compensation for each channel, to select an initial time constant for all channels and the ability to trim the Strength Duration compensation on a per channel basis.
Figure 22C:
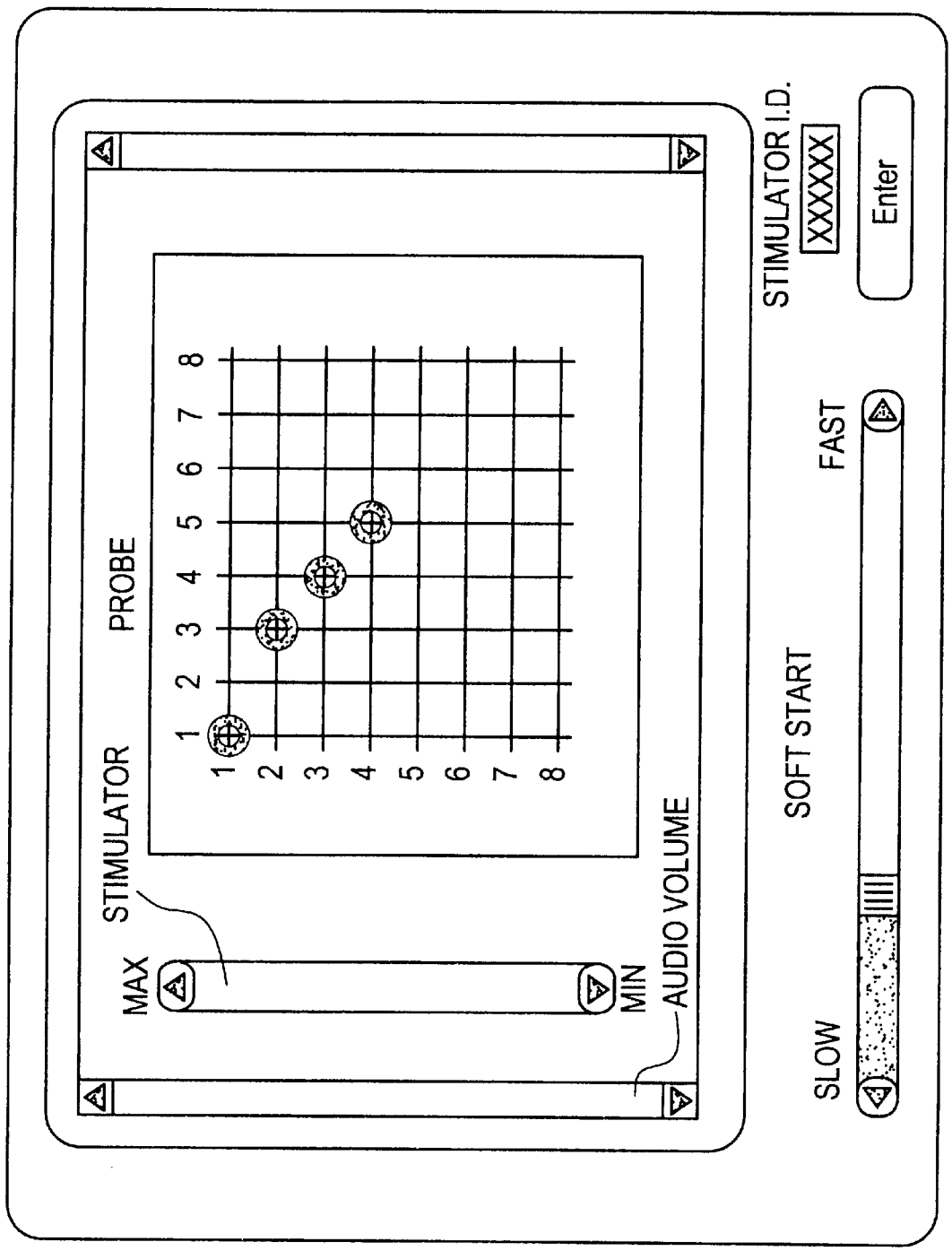
FIG. 22c provides for the ability for the optimum channels from the probe to be connected to the stimulator, to adjust the stimulus level for each channel, to control the rate of soft start, and to enter a Stimulator or I.D. Number for a permanent record in the patient's file.

FIGS. 22A, 22B and 22C are the screen displays for the various functions computer screens.

Figure 21A:
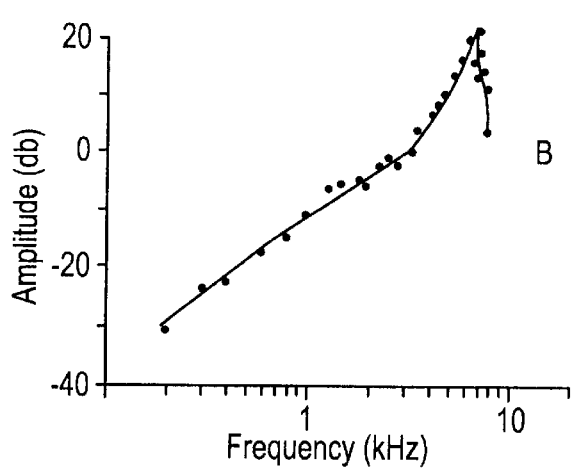
FIG. 21A plots the input-output ratio, in decibels, for the Malleus and Basilar membrane. (Rhode WS: Ann Otol Rhinol Laryngol 86:610–6126, 1974)
Figure 21B:
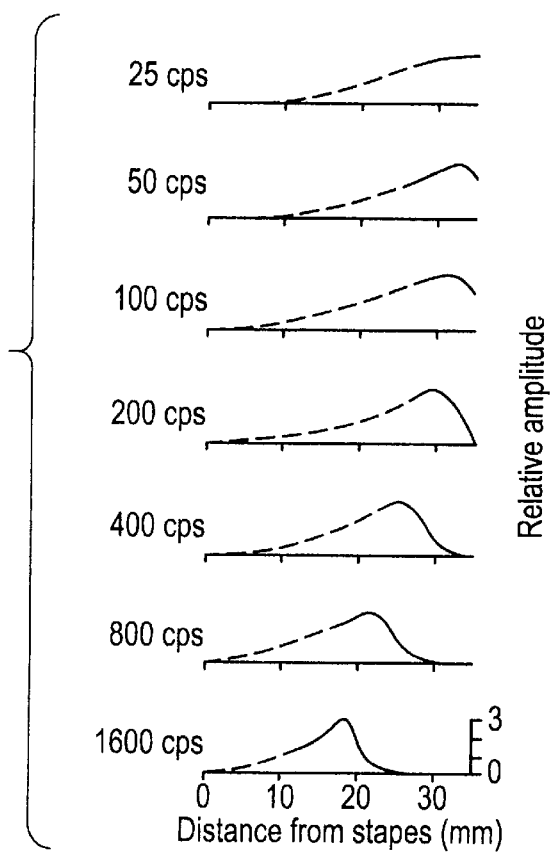
FIG. 21B shows the patterns of vibration of cochlear partition of cadaver specimen for various frequencies. (Beckesy: Experiments in Hearing, New York, McGraw-Hill, 1960.)

In the center of FIG. 21 is the block diagram 130 of the implant unit. To the far left of the block diagram is the receiving/transmitting loop antenna. This feeds to the receiver which develops a voltage that is then regulated and provides component failure protection, power up and down of the embedded microprocessor, high voltage for non-volatile memory writing and a soft start and soft shut down of the probe stimulus. A second output of the receiver is the serial data output. This feeds a data decoder and then the microprocessor. Both command signals and audio data enter the microprocessor. The programed function values of the microprocessor are set into a non-volatile memory. Eight digital to analog converters (these may either be of an analog type or can be produced by pulse width modulation as subthreshold stimulus acts in an additive way and has an effect of increasing the excitability of nerve cell membranes) to drive eight current sources of which four to eight may be used. The outputs of these current sources produce both negative and positive currents to establish an average DC potential of zero. These current source channels are then selected by the electrode switch matrix to feed though capacitors, reducing the possibility of a DC component residue, to the probe electrodes.

As those of ordinary skill in the art will understand, the present invention may be embodied in many different specific ways, and the specific details disclosed herein are only examples of how to practice the invention. For example, many alternate block and circuit diagrams are the equivalent of the example diagrams shown in the drawings, and may be used to perform this invention. Also, the electrical circuits needed may be manufactured as integrated circuits or they may be embodied in a microprocessor, or a combination of integrated circuits and microprocessor may be used. In fact, a microprocessor, because it may be programmable and because of its small size, may be a particularly advantageous device for use in the invention.

While it is apparent that the invention herein disclosed is well calculated to fulfill the objects previously stated, it will be appreciated that numerous modifications and embodiments may be devised by those claims cover all such modifications and embodiments as fall within the true spirit and scope of the present invention.

What is claimed is:

1. A device for applying electrical stimuli to any branch of the 8th nerve, comprising:

a stimulus generator for applying electrical stimuli to nerve fibers of the 8th nerve during at least two time channels so as to produce or enhance a stream of nerve activity at a generally constant rate, independent of audio modulation, that is capable of acting as a carrier wave and that is perceived by the brain as active silence.

2. A device according to claim 1, wherein:

the stimulus generator applies electric fields to at least two groups of nerve fibers to cause fibers in each group to stream at a generally uniform rate.

3. A device according to claim 2, wherein the stimulus generator applies a time varying electric field to each group of fibers that compensates for the strength-duration characteristics of the fibers in the group in order to cause the fibers in the group to stream at said generally uniform rate.

4. A device according to claim 2, wherein the stimulus generator applies a space varying electric field to each group of fibers that compensates for the strength-duration characteristics of the fibers in the group in order to cause the fibers in the group to stream at said generally uniform rate.

5. A device according to claim 2, wherein the stimulus generator includes:

a plurality of electric field generators, each electric field generator being positioned adjacent a respective one of the group of nerve fibers for applying electric fields to said adjacent group of nerve fibers; and a signal generator to apply signals to the electric field generators to cause the electric field generators to apply electric fields to the nerve fibers so as to produce or enhance the stream of nerve activity at the generally constant rate.

6. A device according to claim 1, wherein the stimulus generator includes means to modulate the carrier wave to produce the sensation of sound.

7. A device according to claim 6, wherein:

each stimuli is applied during one of the time channels to an associated group of the nerve fibers;

each time channel includes a latency period and a streaming period;

when one of the stimuli is applied to the associated group of nerve fibers during one of the time channels, the fibers in the associated group of fibers stream at a generally uniform rate during the streaming period of the time channel to produce or to enhance the carrier wave, and the means to modulate the carrier wave modulates said one electric stimuli during the streaming period of said one of the time channels.

8. A device according to claim 2, wherein:
each stimulus is applied during one of the time channels to one of the groups of fibers;
each time channel includes a latency period;
when one of the stimuli is applied to one of the groups of fibers during one of the time channels, said one of the stimuli includes compensation for the strength-duration characteristics of the fibers in said one group to cause the fibers in the group to stream at the generally uniform rate, and said compensation for the strength-duration characteristics occurs after the latency period of said one of the time channels.

9. A device according to claim 1, wherein the stimulus generator applies electric fields to a multitude of sets of nerve fibers to cause fibers in each set to fire substantially simultaneously.

10. A device according to claim 1 wherein the stimulus generator applies stimuli to a multitude of groups of nerve fibers to produce said stream of nerve activity.

11. A device according to claim 10, wherein:
the stimulus generator applies electric fields to the groups of nerve fibers to cause fibers in each group to stream at a generally uniform rate.

12. A device according to claim 11, wherein:
the stimulus generator applies electric fields to each of the groups of nerve fibers for a respective one time channel and in a defined sequence, and wherein channels adjacent in time overlap in time to compensate for a latency period in the firing of nerve fibers.

13. A device according to claim 12, wherein pairs of channels adjacent in time overlap for a substantially constant length of time.

14. A device according to claim 12, wherein:
over a defined cycle time, the stimulus generator applies electric fields to a number of the groups of fibers; and
in such defined cycle time, the stimulus generator does not apply electric fields to each group of fibers for a rest period of time to provide the nerve fibers in each group with a recovery time.

15. A device according to claim 12, wherein:
over a defined cycle time, the stimulus generator applies electric fields to a given number of the groups of fibers; and
in such defined cycle time, the stimulus generator applies electric fields to all said given number of the groups of fibers for a generally equal length of time.

16. A device for applying electrical stimuli to any branch of the 8th nerve, comprising:
a stimulus generator for applying electrical stimuli to a multitude of sets of nerve fibers of the 8th nerve during a multitude of time channels, to cause the fibers in each set to fire substantially simultaneously and to produce a stream of nerve activity at a generally constant rate, independent of audio modulation, that is capable of acting as a carrier wave and that is perceived by the brain as active silence.

17. A device according to claim 16, wherein the amplitude of the electrical stimulus is such that each set of fibers fires within about 120 microseconds after one of the stimulus is applied to the set of fibers.

18. A device according to claim 16, wherein:
the stimulus generator applies electric fields to each of the sets of nerve fibers during a respective one time channel and in a defined sequence, and wherein channels adjacent in time overlap in time to compensate for a latency period in the firing of the nerve fibers.

19. A device for applying electrical stimuli to a branch of the 8th cranial nerve, comprising in combination:
means for stimulation of a number (N) of different groups of nerve fibers of the 8th cranial nerve, said groups of nerve fibers being phased in N spaced intervals; and
means for repeatedly applying electric fields to the fiber groups to produce or enhance a constant stream of nerve activity, independent of audio modulation, that is capable of acting as a carrier wave and that is perceived by the brain as active silence; and wherein the carrier wave, when modulated, results in the perception of sound; and
wherein, for each fiber group, an interval is provided between applications of the electric fields to the fiber group, and said interval is not less than the natural recover time of the nerve fibers in the group.

20. A device according to claim 19, wherein:
the means to apply the electric fields applies a time varying electric field to each group of fibers that compensates for the strength-duration characteristics of the fibers in the group in order to cause the fibers in the group to stream at a generally uniform rate.

21. A device according to claim 20, wherein:
the means to apply the electric fields applies electric fields to pairs of groups of fibers for an overlapping period of time to compensate for a latency period in the firing of nerve fibers.

22. A method for applying electrical stimuli to a branch of the 8th cranial nerve, comprising:
using a stimulus generator to apply electrical stimuli to nerve fibers of the 8th cranial nerve during at least two time channels so as to produce or enhance a stream of nerve activity at a generally constant rate, independent of audio modulation, that is capable of acting as a carrier wave and that is perceived by the brain as active silence.

23. A method according to claim 22, wherein:
the step of using the stimulus generator includes the step of applying electric fields to at least two groups of nerve fibers to cause fibers in each group to stream at a generally uniform rate.

24. A method according to claim 23, wherein the step of using the stimulus generator further includes the step of applying a time varying electric field to each group of fibers that compensates for the strength duration characteristics of the fibers in the group in order to cause the fibers in the group to stream at said generally uniform rate.

25. A method according to claim 23, wherein the step of using the stimulus generator includes the steps of:
positioning a respective one electric field generator adjacent each of the groups of nerve fibers for applying electric fields to said adjacent group of nerve fibers; and
using a signal generator to apply signals to the electric field generators to cause the electric field generators to apply electric fields to the nerve fibers so as to produce said generally constant stream of nerve activity.

26. A method according to claim 22, further comprising the step of modulating the carrier wave to produce the sensation of sound.

27. A method according to claim 22, wherein the step of using the stimulus generator includes the step of applying stimuli to a multitude of channels of fibers to produce said stream of nerve activity.

28. A method according to claim 27, wherein the step of using the stimulus generator includes the steps of:
applying electric fields to each of the groups of nerve fibers for a respective one time channel and in a defined sequence; and overlapping adjacent channels in time to compensate for a latency period in the firing of nerve fibers.

29. A method according to claim 28, wherein pairs of channels adjacent in time overlap for a substantially constant length of time.

30. A method according to claim 28, wherein the step of using the stimulus generator further includes the steps of:

over a defined cycle time, applying electric fields to a number of the groups of fibers; and in such defined cycle time, providing each group of fibers with a rest period, wherein the electric fields are not applied to the group of fibers, to provide the nerve fibers in each group with a recovery time.

31. A method according to claim 28, wherein:

over a defined cycle time, the stimulus generator applies electric fields to a given number of the groups of fibers; and in such defined cycle time, the stimulus generator applies electric fields to all said given number of the groups of fibers for a generally equal length of time.

32. A method of directly stimulating nerve fibers of the 8th cranial nerve with electrical signals representative of sensed audio sounds in sequence to impart the sensation of hearing to a deaf patient, the method comprising the steps of:

implanting in the patient a receiver with an antenna and with connections to an electrode probe, comprised of an array of electrodes formed to produce multiple gradient fields in the area of the cochlear nerve;

generating an electrical signal representative of sensed audible sounds;

dividing the electrical signal into time multiplexed channels, wherein each multiplexed channel is connected to a corresponding gradient probe channel and contains the audible representation of the entire audio spectrum and means for limiting the audio spectrum;

processing each channel to produce a bi-phasic stimulation signal that overlaps a time adjacent channel bi-phasic stimulation signal but does not overlap its component that is representative of audible sounds;

aligning an external transmitter/receiver antenna with the implanted antenna such that there is a distance at least equal to the thickness of the patient's skin separating the external antenna from the internal antenna, wherein said external antenna provides a means of transmitting both power and audible sound representations to the implanted receiver;

locating the gradient probe in proximity to the nerve fibers that transmit sound sensations to the brain; and permanently fixing the gradient probe in place in the patient.

\* \* \* \* \*